United States Patent
Vogt et al.

(10) Patent No.: US 11,039,872 B2
(45) Date of Patent: Jun. 22, 2021

(54) DEVICE FOR STORAGE, MIXING AND DISPENSING OF A BONE CEMENT, AND PERTINENT METHOD

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 377 days.

(21) Appl. No.: 15/945,355

(22) Filed: Apr. 4, 2018

(65) Prior Publication Data

US 2018/0289406 A1   Oct. 11, 2018

(30) Foreign Application Priority Data

Apr. 7, 2017   (DE) .......................... 102017107569.0

(51) Int. Cl.
*A61B 17/88*   (2006.01)
*B01F 5/06*   (2006.01)
(Continued)

(52) U.S. Cl.
CPC ...... *A61B 17/8833* (2013.01); *A61B 17/8825* (2013.01); *A61L 24/02* (2013.01);
(Continued)

(58) Field of Classification Search
CPC ............ A61B 17/8802; A61B 17/8805; A61B 17/8822; A61B 17/8825; A61B 17/8827;
(Continued)

(56) References Cited

U.S. PATENT DOCUMENTS 2,446,501 A   8/1948   Weber
3,682,174 A   8/1972   Cohen
(Continued)

FOREIGN PATENT DOCUMENTS

CN   101835434 A   9/2010
DE   2939953 A1   4/1981
(Continued)

OTHER PUBLICATIONS

Charnley, John "Anchorage of the femoral head prosthesis of the shaft of the femur" J Bone Joint Surg, 1960, 42, pp. 28-30.

*Primary Examiner* — Si Ming Ku
(74) *Attorney, Agent, or Firm* — Stradley Ronon Stevens & Young, LLP

(57) ABSTRACT

A device for storage of a monomer liquid and a cement powder as starting components of a bone cement dough and for mixing the starting components, and for dispensing the mixed bone cement dough. The device includes a receptacle in which a monomer liquid container is arranged and a cartridge containing the cement powder. A feed plunger is arranged in the receptacle. A dispensing plunger is arranged between the monomer liquid container and the cement powder in the cartridge. The feed plunger can be punctured by a rod when motion of the feed plunger is blocked, whereby the dispensing plunger is propelled by propelling the rod further through the blocked and punctured feed plunger.
Also provided are an extrusion device for propelling a feed plunger and a dispensing plunger of a device for mixing of a bone cement dough, and a method for the production of a bone cement dough.

28 Claims, 15 Drawing Sheets

(51) Int. Cl.
*B01F 15/02* (2006.01)
*B01F 13/00* (2006.01)
*A61L 24/02* (2006.01)
*A61L 24/06* (2006.01)
*C04B 26/06* (2006.01)
*A61M 5/28* (2006.01)
*A61M 5/315* (2006.01)
*C04B 111/00* (2006.01)

(52) U.S. Cl.
CPC ............ *A61L 24/06* (2013.01); *B01F 5/0615* (2013.01); *B01F 13/0023* (2013.01); *B01F 15/0206* (2013.01); *B01F 15/0237* (2013.01); *C04B 26/06* (2013.01); *A61B 2017/8838* (2013.01); *A61M 5/284* (2013.01); *A61M 2005/31598* (2013.01); *C04B 2111/00836* (2013.01)

(58) Field of Classification Search
CPC ............ A61B 17/8833; A61B 17/8836; B01F 13/0023; B01F 15/0206; B01F 15/0207; B01F 15/0237
See application file for complete search history.

(56) References Cited

U.S. PATENT DOCUMENTS

| | | | |
|---|---|---|---|
| 3,739,947 A | 6/1973 | Baumann et al. | |
| 3,785,379 A * | 1/1974 | Cohen | A61M 5/31596 604/88 |
| 4,463,875 A | 8/1984 | Tepic | |
| 4,613,326 A | 9/1986 | Szwarc | |
| 4,671,263 A | 6/1987 | Draenert | |
| 4,758,096 A | 7/1988 | Gunnarsson | |
| 4,973,168 A | 11/1990 | Chan | |
| 4,994,065 A | 2/1991 | Gibbs et al. | |
| 5,026,283 A | 6/1991 | Osanai et al. | |
| 5,100,241 A | 3/1992 | Chan | |
| 5,344,232 A | 9/1994 | Nelson et al. | |
| 5,501,520 A | 3/1996 | Lidgren et al. | |
| 5,551,778 A | 9/1996 | Hauke et al. | |
| 5,586,821 A | 12/1996 | Bonitati et al. | |
| 5,588,745 A | 12/1996 | Tanaka et al. | |
| 5,624,184 A | 4/1997 | Chan | |
| 5,685,846 A | 11/1997 | Michaels, Jr. | |
| 5,997,544 A | 12/1999 | Nies et al. | |
| 6,033,105 A | 3/2000 | Barker et al. | |
| 6,676,663 B2 | 1/2004 | Higueras | |
| 6,709,149 B1 | 3/2004 | Tepic | |
| 6,871,996 B2 | 3/2005 | Jonsson | |
| 6,935,541 B1 | 8/2005 | Campbell et al. | |
| 7,008,433 B2 | 3/2006 | Voellmicke et al. | |
| 7,112,205 B2 | 9/2006 | Carrison | |
| 8,038,682 B2 | 10/2011 | McGill et al. | |
| 8,308,731 B2 | 11/2012 | Valaie | |
| 8,348,494 B2 | 1/2013 | Melsheimer et al. | |
| 8,544,683 B2 | 10/2013 | Springhorn et al. | |
| 8,690,419 B2 * | 4/2014 | Faccioli | A61B 17/8833 366/139 |
| 9,005,209 B2 | 4/2015 | Click et al. | |
| 2003/0014056 A1 | 1/2003 | Tague et al. | |
| 2004/0074927 A1 | 4/2004 | Lafond | |
| 2008/0086143 A1 | 4/2008 | Seaton et al. | |
| 2008/0312588 A1 | 12/2008 | Faccioli et al. | |
| 2008/0319445 A9 | 12/2008 | McGill et al. | |
| 2011/0027751 A1 | 2/2011 | Kojima et al. | |
| 2011/0112543 A1 | 5/2011 | Palazzolo et al. | |
| 2011/0272433 A1 | 11/2011 | Vogt et al. | |
| 2012/0155214 A1 | 6/2012 | Faccioli et al. | |
| 2016/0045283 A1 | 2/2016 | Boehm et al. | |
| 2016/0100875 A1 | 4/2016 | Faccioli et al. | |

FOREIGN PATENT DOCUMENTS

| | | |
|---|---|---|
| DE | 3640279 A1 | 6/1987 |
| DE | 3723985 A1 | 2/1988 |
| DE | 9215566.9 U1 | 11/1993 |
| DE | 69812726 T2 | 2/2004 |
| DE | 202005010206 U1 | 9/2005 |
| DE | 102005045227 A1 | 3/2007 |
| DE | 102009031178 B3 | 9/2010 |
| DE | 102010019223 A1 | 11/2011 |
| EP | 0692229 A1 | 1/1996 |
| EP | 0796653 A2 | 9/1997 |
| EP | 1005901 A2 | 6/2000 |
| EP | 1016452 A2 | 7/2000 |
| EP | 1020167 A2 | 7/2000 |
| EP | 1074231 B1 | 4/2003 |
| EP | 1596736 B1 | 8/2006 |
| EP | 1464292 B1 | 7/2007 |
| EP | 1886647 A1 | 2/2008 |
| EP | 1614403 B1 | 11/2010 |
| EP | 2730296 A2 | 5/2014 |
| JP | 2011067265 | 4/2011 |
| WO | 94/26403 A1 | 11/1994 |
| WO | 99/67015 A1 | 12/1999 |
| WO | 00/35506 A1 | 6/2000 |
| WO | 00/45732 | 8/2000 |
| WO | 2008/038322 A2 | 4/2008 |
| WO | 2008/097855 A2 | 8/2008 |
| WO | 2016/166711 | 10/2016 |

* cited by examiner

FIG. 3c
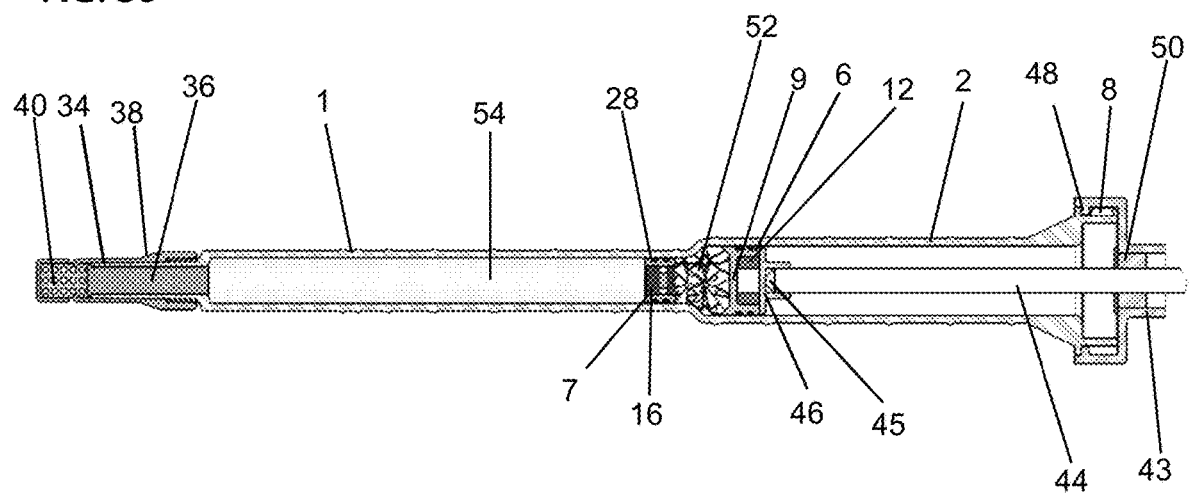
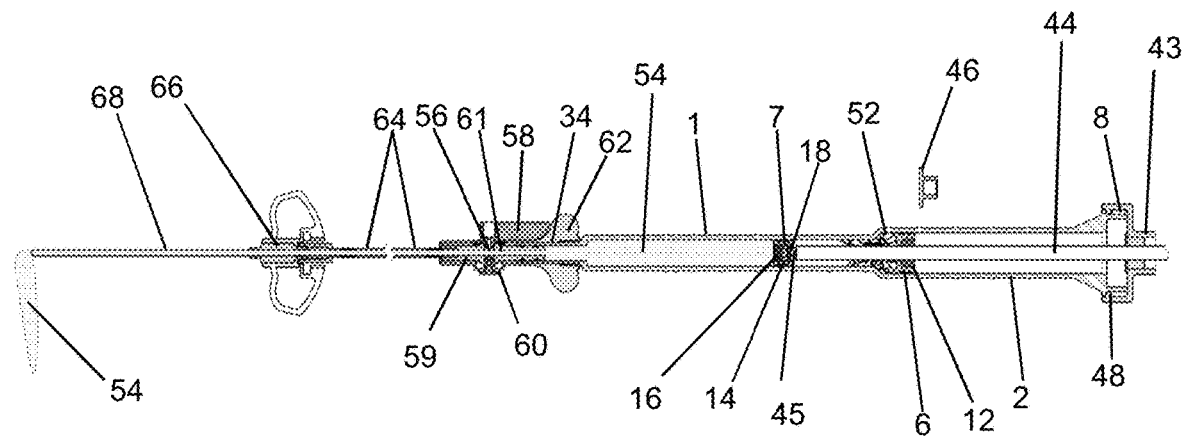
FIG. 3d

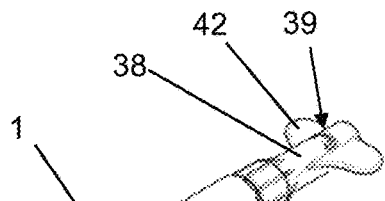
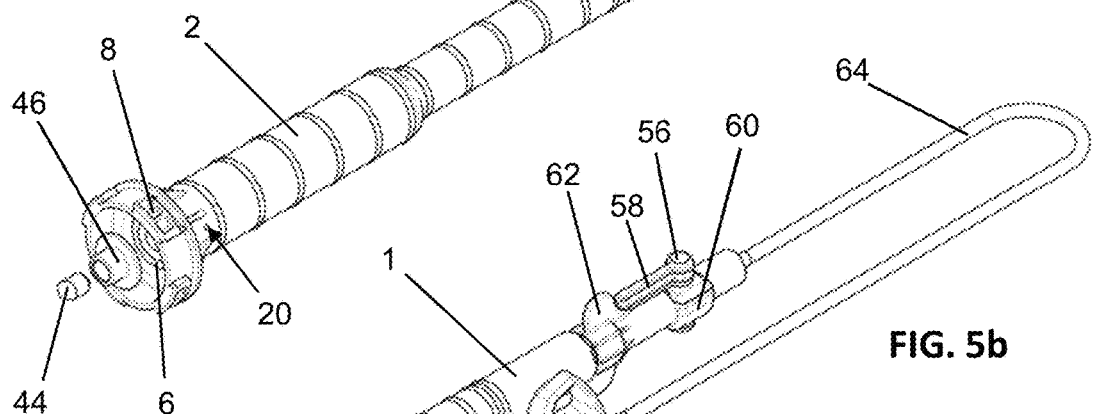
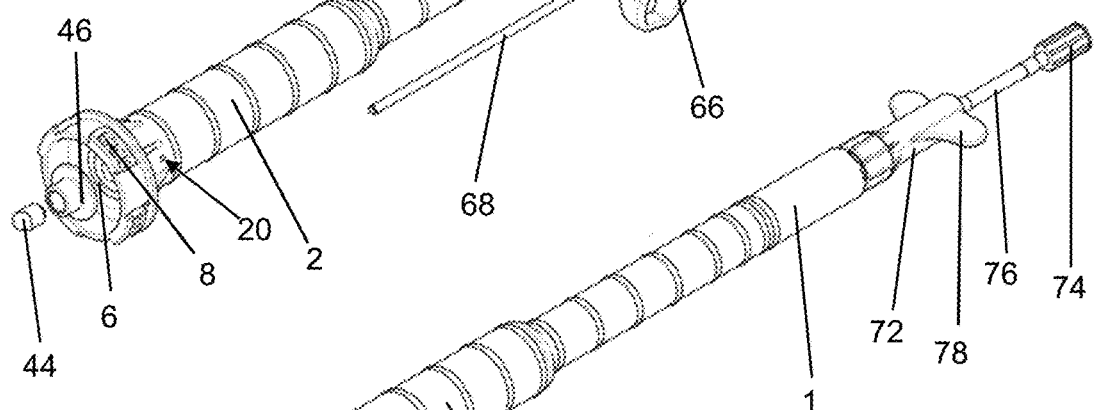
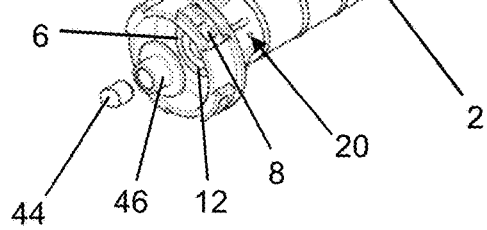

DEVICE FOR STORAGE, MIXING AND DISPENSING OF A BONE CEMENT, AND PERTINENT METHOD

RELATED APPLICATION

This application claims priority of German Patent Application No. DE 10 2017 107 569.0 filed on Apr. 7, 2017.

TECHNICAL FIELD

The invention relates to a device for storage of a monomer liquid and a cement powder as starting components of a bone cement dough and for mixing of the bone cement dough from the starting components, and for dispensing the mixed bone cement dough.

The invention also relates to an extrusion device for application of said device and to a method for the production of a bone cement dough, in particular of a pasty polymethylmethacrylate bone cement dough.

BACKGROUND OF THE INVENTION

The subject matter of the invention specifically is a device for separate storage of the cement powder and the monomer liquid of polymethylmethacrylate (PMMA) bone cements, for subsequent mixing of the cement powder with the monomer liquid in order to produce a bone cement dough, and for dispensing the mixed bone cement dough. The bone cement dough produced with the device is designed, in particular, for augmentation of fractured vertebral bodies, i.e., for vertebroplasty or kyphoplasty. The device according to the invention is a full-prepacked cementing system.

PMMA bone cements are based on the pioneering work of Sir Charnley (Charnley, J.: Anchorage of the femoral head prosthesis of the shaft of the femur. J. Bone Joint Surg. 42 (1960) 28-30.). Conventional PMMA bone cements (PMMA bone cements) are made from a powdered component and a liquid monomer component (K.-D. Kühn: Knochenzemente für die Endoprothetik: Ein aktueller Vergleich der physikalischen and chemischen Eigenschaften handelsüblicher PMMA-Zemente. Springer-Verlag Berlin Heidelberg New York, 2001). The powder component, also called cement powder or bone cement powder, comprises one or more polymers that are produced through polymerization, preferably suspension polymerization, based on methylmethacrylate and co-monomers, such as styrene, methylacrylate or similar monomers, a radiopaquer, and the initiator dibenzoylperoxide. Upon mixing the powder component and the monomer component, swelling of the polymers of the powder component in the methylmethacrylate generates a dough that can be shaped plastically and is the actual bone cement. During the mixing of powder component and monomer component, the activator, N,N-dimethyl-p-toluidine, reacts with dibenzoylperoxide while forming radicals. The radicals thus formed trigger the radical polymerization of the methylmethacrylate. Upon advancing polymerization of the methylmethacrylate, the viscosity of the cement dough increases until the cement dough solidifies.

A number of special PMMA bone cements have been developed for treatment of impression fractures of vertebral bodies. These are characterized in that they contain a relatively high fraction of radiopaquer, for example zirconium dioxide or barium sulfate. This is to facilitate continuous monitoring of the spreading of the bone cement dough in the fractured vertebra by fluoroscopy. Vertebroplasty and kyphoplasty are the processes for augmentation of fractured vertebral bodies used most commonly today. Currently, manual mixing of the cement components in mixing beakers or in simple mixing devices is common in this context.

PMMA bone cements can be mixed by mixing the cement powder and the monomer liquid in suitable mixing beakers with the aid of spatulas. This can lead to air bubbles being enclosed in the bone cement dough, which can have a negative effect on the mechanical properties of the cured bone cement.

A large number of vacuum cementing systems has been described for preventing air inclusions in bone cement dough of which the following are specified here for exemplary purposes: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, EP 1 886 647 A1, and U.S. Pat. No. 5,344,232 A.

Cementing systems, in which both the cement powder and the monomer liquid are already packed in separate compartments of the mixing devices and are mixed with each other in the cementing system only right before application of the cement, are a development of cementing technology. Said closed full-prepacked mixing devices have been proposed in EP 0 692 229 A1, DE 10 2009 031 178 B3, U.S. Pat. Nos. 5,997,544 A, 6,709,149 B1, DE 698 12 726 T2, EP 0 796 653 A2, and U.S. Pat. No. 5,588,745 A.

Patent DE 10 2009 031 178 B3 discloses a storage and mixing device as a full-prepacked mixing device, in which the starting components required for the production of the bone cement dough are stored initially in the storage and mixing device and can be combined and mixed in the storage and mixing device. The storage and mixing device comprises a two-part dispensing plunger for closing a cement cartridge. A combination of a gas-permeable sterilization plunger and a gas-impermeable sealing plunger is used in this context.

After mixing the cement powder with the liquid monomer component, PMMA bone cements are applied in their non-cured pasty state in the form of a cement dough. If mixing devices are used with powder-liquid cements, the cement dough is situated in a cartridge. The cement dough is squeezed from said cartridge by moving a dispensing plunger. The dispensing plungers usually have a diameter of between 30 mm and 40 mm and thus have a surface area of 7.0 $cm^2$ to 12.5 $cm^2$ on the outside that is engaged by the pestle and/or a rod of the extrusion device during the extrusion process. The motion of the dispensing plunger is effected by manually operated mechanical extrusion devices, which are also called applicators. Said manual extrusion devices usually reach an extrusion force in the range of approximately 1.5 kN to 3.5 kN.

The application of conventional PMMA bone cements, which consist of a liquid monomer component and a separately stored cement powder component as starting components, involves the two starting components being mixed in cementing systems and the cement dough thus formed then being extruded by manually operated extrusion devices. These simple mechanical extrusion devices utilize, in particular, clamp rods that are driven by a manually actuated tilting lever for extrusion. The manually driven extrusion devices are time-proven throughout the world for decades and as such are the current prior art. Said extrusion devices are advantageous in that the medical user has a feel for the penetration resistance of the bone cement dough into the bone structures (cancellous bone) by the manual force to be expended.

The use of all full-prepacked mixing devices known to date requires the medical user to perform multiple working steps on the devices in a predetermined order, one after the other, until the bone cement dough is ready-mixed and can be applied. Any confusion of the working steps can lead to failure of the mixing device and can therefore cause a disturbance in the surgical procedure. Cost-intensive training of the medical users is therefore required in order to prevent user errors from occurring.

WO 00/35506 A1 proposes a device, in which the PMMA cement powder is stored in a cartridge, whereby the cement powder takes up the entire volume of the cartridge and the volume of the intervening spaces between the particles of the cement powder is equal to the volume of the monomer liquid required for the production of bone cement dough using the cement powder stored in the cartridge. The design of said device assures that the action of a vacuum causes the monomer liquid to be supplied into the cartridge from above, whereby a vacuum is applied to a vacuum connector on the underside of the cartridge for this purpose. As a result, the monomer liquid is aspirated through the cement powder, whereby the air present in the intervening spaces of the cement powder particles is replaced by the monomer liquid. This involves no mechanical mixing of the cement dough thus formed by a stirrer.

It is a disadvantage of the system that cement powders, which swell quickly due to the monomer liquid, cannot be mixed with said device, because the rapidly swelling cement powder particles form a gel-like barrier of approximately 1 to 2 cm after ingress of the monomer liquid into the cement powder and impede the migration of the monomer liquid through the entire cement powder. Moreover, conventional cement powders show a phenomenon, which is that the cement powder particles are wetted only poorly by methylmethacrylate due to the difference in surface energies. As a result, the methylmethacrylate penetrates only slowly into the cement powder. Moreover, it cannot be excluded that the monomer liquid, exposed to the action of a vacuum, is aspirated through the vacuum connector after the monomer liquid fully penetrates into the cement powder. In this case, an insufficient amount of monomer liquid for curing by radical polymerization is available and/or the mixing ratio and thus the consistency of the bone cement is changed inadvertently. Moreover, it is a problem that the air trapped between the cement powder particles is to be displaced by the monomer liquid proceeding from top to bottom, because the air, having a lower specific weight than the monomer liquid, tends to migrate upwards in the cement powder rather than downwards in the direction of the vacuum connector under the force of gravity.

In the case of high viscosity pasty bone cements used with cartridges, in which the dispensing plunger has a total surface area in the range of 7.0 cm$^2$ to 12.5 cm$^2$ at the external plunger side, which is engaged by a pestle and/or a rod of the extrusion devices, these devices can be operated manually either not at all or only while expending a very large force. This is true even more if the flow resistance of the bone cement dough to be extruded is increased by a hose or a trocar as an extended dispensing opening and/or by a static mixer, as is common in applications at the spine, in which the bone cement dough is dispensed via a hose or a trocar. This exertion of a large force is unreasonable for medical users in the operating room or OR.

From the adhesives and sealants industry, electrically driven extrusion devices are known as well. Said devices can be driven both with rechargeable batteries and by a stationary electrical power supply. Said devices can extrude particularly thick pasty masses since their extrusion force is very large in some cases. However, it is one disadvantage of the use of electrical motors that these motors contain non-ferrous metals and are expensive purchases. Since the OR area needs to be kept sterile, said devices need to be sterilized with much effort or may even need to be replaced. The presence of electrical wiring may impede the mobility of the user in the OR.

Moreover, pneumatic devices have been proposed as well. Said devices require a stationary or mobile compressed air connection (e.g., U.S. Pat. No. 2,446,501 A, DE 20 2005 010 206 U1). This necessitates compressed air hoses, which may impede the mobility of the user.

Alternatively, the use of compressed gas cartridges to provide compressed gas is feasible just as well. Devices have been proposed for this purpose, in which the supply of compressed gas is controlled by a valve and, in addition, the flow of the viscous mass is controlled by a second valve (e.g., US 2004/0074927 A1, U.S. Pat. No. 6,935,541 B1). These devices have the gas cartridges integrated into the devices. These systems, which are connected to compressed air or contain compressed gas cartridges, always necessitate the presence of a compressed gas source in the absence of which the systems cannot be used.

In vertebroplasty, the application of bone cement is monitored in situ by an x-ray procedure. Application devices for vertebroplasty usually have a hose inserted in them through the tip of which the bone cement can be applied to allow the user to work outside the range of the x-rays. For this purpose, a trocar or a cannula can be arranged as well on the hose. Said systems are known, for example, from U.S. Pat. No. 7,112,205 B2, U.S. Pat. No. 8,038,682 B2, U.S. Pat. No. 8,308,731 B2, DE 10 2005 045 227 A1, EP 1 074 231 B1, EP 1 596 736 B1, U.S. Pat. No. 9,005,209 B2, and WO 2008/097855 A2.

Alternatively, other set-ups can be used for keeping the user away from the x-rays, such as are described, for example, in documents U.S. Pat. No. 6,676,663 B2, U.S. Pat. No. 7,008,433 B2, U.S. Pat. No. 8,348,494 B2, EP1 464 292 B1, EP 1 614 403 B1, US 2008/319445 A9, and WO 2008/038322 A2.

A bone cement applicator for vertebroplasty for application of bone cement comprising a hose, a trocar, and a mixer is known from US 2008/0086143 A1. The bone cement applicator comprises two cartridges arranged next to each other, in which the starting components are stored as well. The bone cement applicator is assembled right before use. In bone cement applicators for vertebroplasty of this type, pressure is exerted on the starting components of the bone cement by an extrusion device propelling the dispensing plungers in the cartridges, and the pressure is used to expel the starting components from the cartridges and through the hose. In this context, the starting components are usually mixed first in an upstream static mixer. As a result, the parts of the bone cement applicator serving as borders to the bone cement flow (the cartridges, the housing of the mixer, and the hose) are subject to elastic deformation. When the propulsion of the dispensing plunger is stopped, the elastic force of said parts leads to a volume contraction of said parts such that bone cement continues to exit through the application opening of the hose and/or trocar. This may lead to contamination of the operation room (OR) or of the user with bone cement or an excessive amount of the bone cement is applied inadvertently. Moreover, when the volume flow of the bone cement dough is to be started up again, pressure needs to be established in the bone cement first to make the bone cement exit through the application opening.

This, in turn, delays the time point after commencement of the propulsion of the dispensing plungers from which the bone cement can actually be applied, which is also undesirable. Since the bone cement dough and the starting components are highly viscous, in particular where pasty starting components are used, all these effects are relatively strongly pronounced. This can be counteracted by the use of massive and expensive metallic housing parts. Said parts need to be cleaned after use and need to be sterilized for further use or need to be recycled with much effort. Moreover, residual starting components may be released when the cartridges are taken off and may contaminate the OR theater.

U.S. Pat. No. 8,544,683 B2 discloses a cartridge system that is suitable for admixing a small amount to a main starting component. The cartridge system has a second smaller cartridge arranged adjacent to a cartridge, whereby, along with the propulsion of a dispensing plunger in the larger cartridge, a dispensing plunger in the smaller cartridge is also driven by a joint connecting element. However, the system is not suitable for mixing the viscous pasty starting components of PMMA bone cement.

SUMMARY OF THE INVENTION

Accordingly, it is the object of the present invention to overcome the disadvantages of the prior art. In particular, it is the object of the invention to develop a device that is well-suited for storage of a monomer liquid and a cement powder as starting components of a bone cement dough, and for mixing the bone cement dough from the starting components, and for dispensing the mixed bone cement dough, and an extrusion device that is well-suited for application of said device, and a method for the production of a bone cement dough, in particular of a pasty PMMA bone cement dough, whereby the bone cement dough is produced from a cement powder and a monomer liquid through the use of said device.

It shall be feasible to drive the device by a simple extrusion device, and the device is to be as easy as possible to operate. The design is to be inexpensive to allow the device to be used just a single time for hygienic reasons. As many as possible or all of the processes taking place in the device, such as the mixing of the starting components, the dispensing of the bone cement dough, and the opening of containers and, if applicable, of the cartridge, are to take place in the smallest possible number of working steps and are to be automated to the extent possible and preferably are to be driven by a single drive only.

Accordingly, it is also an object of the invention to develop a device for storage and mixing of cement powder and monomer liquid, whereby the PMMA bone cement dough produced by mixing the cement components is preferably intended for augmentation of fractured vertebral bodies. The handling of the device is to be maximally simplified in order to basically prevent user errors resulting from assembly steps taking place incorrectly. The medical user is to be enabled, after taking it out of a packaging, to connect the device to an extrusion device and to subsequently manually actuate said facility. Additional assembly and working steps are to be omitted due to the design of the device. The device is to ensure the secure storage of cement powder and monomer liquid in separate compartments such that any inadvertent mixing of the cement components during storage of the device is excluded. The device is to allow for sterilization with ethylene oxide gas. For this purpose, the cement powder stored in the device must be accessible to ethylene oxide. It shall be feasible to activate the device with the aid of a manually driven extrusion device in the OR such that, after form-fitting or force-locked connection of the device to the extrusion device, the axially propellable rod of the extrusion device acts on the device due to the extrusion device being actuated and opens the monomer liquid container and subsequently, when the rod moves further, transfers the monomer liquid into the cement powder. The mixing of the monomer liquid and the cement powder is to take place without the aid of a mixer that is to be moved manually from outside. Just the forward motion of the rod of the extrusion device, if possible, is to effect the opening of the monomer liquid container, the subsequent monomer transfer into the cement powder, and the mixing of the cement components while forming the bone cement dough. Moreover, it is important for application in vertebroplasty that a suitable connector or a connector with a hose, through which the bone cement dough produced can be applied, can be attached to the device. It is also important for this kind of application to design the plunger for dispensing the bone cement dough thus produced appropriately such that the pressure acting on the plunger upon the use of a manual extrusion device is sufficiently high such that the bone cement dough can be extruded through a plastic hose with an internal diameter of 3 mm over a distance of at least 20 cm.

Preferably, the invention is to also provide a simple and inexpensively manufactured bone cement applicator for vertebroplasty for pasty multicomponent PMMA bone cements and a method for the application of a bone cement dough with a device of this type that has a simple design and is inexpensive to manufacture, whereby the bone cement dough does not continue to flow once the bone cement flow is stopped or interrupted. Moreover, it shall be possible to use the device again as soon as possible after interruption of the flow of bone cement dough. Contamination of the surroundings and of the user by bone cement dough or the starting components, in particular by the monomer liquid, shall be excluded to the extent possible.

It shall be possible to easily manufacture the device from plastics and thus the device shall be suitable as a product for single use. It shall be possible to extrude the mixed cement dough with a conventional manually driven extrusion device of the type that is hitherto conventional for use with PMMA bone cements for the cementing of knee and hip TEP (total endoprosthesis of the hip joint). The bone cement applicator is to be designed appropriately such that an immediate emergency stop of the flowing bone cement dough is feasible without contamination of the surgical theater (OR) by the bone cement dough and/or continued flow of bone cement dough taking place.

Preferably, the bone cement applicator shall not necessitate two rods that are connected to each other and are propelled synchronously in order for the entire device not to become significantly more extensive, longer, and larger than the mixing devices that are thus far customary for the conventional powder-liquid PMMA bone cements. The aim is to find a simple solution that allows the bone cement dough to be extruded, if possible, with an extrusion device that comprises just one rod and, if applicable, a cup connected to it.

The objects of the invention are met by a device for storage of a monomer liquid and a cement powder as starting components of a bone cement dough and for mixing of the bone cement dough from the starting components, and for dispensing the mixed bone cement dough, the device comprising:

a tube-shaped container that forms, on its rear side, a receptacle with a cylindrical internal space, in which a monomer liquid container is arranged, whereby the monomer liquid container contains the monomer liquid, and the container forms, on its front side, a cartridge with a cylindrical internal space that contains the cement powder, whereby a feed plunger which is movable in a longitudinal direction of the receptacle and which is accessible from a rear side of the receptacle is arranged in the internal space of the receptacle, whereby a dispensing plunger which is movable in a longitudinal direction in the internal space of the cartridge is arranged between the monomer liquid container and the cement powder in the internal space of the cartridge, whereby the internal space of the receptacle and the internal space of the cartridge are connected to each other through a connection that is permeable to the monomer liquid and to gases, but is impermeable to the cement powder, and whereby the feed plunger is adapted to be punctured, from the rear side, by a rod, when a motion of the feed plunger in the direction of the front side of the container is blocked, whereby the dispensing plunger is adapted to be propelled by propelling the rod further through the blocked and punctured feed plunger in the direction of a front side of the cartridge.

The device is preferably used for vertebroplasty or kyphoplasty. Accordingly, the invention provides the device to be a bone cement applicator for application of the bone cement dough in the area of the spine, whereby the bone cement applicator preferably comprises an extended dispensing opening that is arranged at the front side of the cartridge, whereby the extended dispensing opening preferably is implemented by a dispensing tube, a hose, and/or a trocar.

The invention can preferably provide the feed plunger to be impermeable to liquids and gases and to close off the receptacle on its rear side in a liquid-tight and gas-tight manner.

The internal space of the cartridge and the internal space of the receptacle each have a cylindrical geometry. The cylindrical shape is the simplest shape by which the internal space of the cartridge and the internal space of the receptacle can be implemented. A cylindrical shape shall be understood geometrically to mean the shape of a general cylinder of any footprint, i.e., not just a cylinder having a circular footprint. Accordingly, the internal wall of the internal space of the cartridge and the internal wall of the internal space of the receptacle can be realized by the cylinder jacket of a cylinder of any footprint, in particular of different footprints, including non-circular or non-round footprints. However, according to the invention, a cylindrical geometry with a rotationally symmetrical and, in particular, circular footprint is preferred for both internal spaces, since these are the easiest to manufacture.

The rod is preferred to be cylindrical, but can comprise a rounded, pointed, or preferably a blunt tip or edge, on the one hand in order to facilitate the puncturing of the feed plunger and, on the other hand, to drive the dispensing plunger without also puncturing the dispensing plunger or deforming it to the extent such that it is no longer movable in the cartridge in the direction of the front side of the cartridge.

For simplicity reasons, the bone cement dough shall be considered to be mixed in the scope of the present invention when the monomer liquid has fully permeated the cement powder and starts to swell in the process. For complete mixing throughout and to attain the absence of tackiness, it may be necessary or helpful to have, additionally, a sufficient amount of time elapse and/or to additionally mix the bone cement dough mechanically, for example through a static mixer. In particular in devices for application in vertebroplasty, the shearing forces occurring when the bone cement dough is extruded through the extended and usually thin application tip (e.g., such as a hose and a trocar) already effect complete mixing of the bone cement dough.

Because the feed plunger is accessible from a rear side of the receptacle, a rod and/or a pestle of an extrusion device, such as, for example, a cartridge gun, can push onto the feed plunger from the rear.

The invention can preferably provide the device to be designed appropriately, in particular the design of the bearing of the dispensing plunger in the internal space of the cartridge, such that the dispensing plunger can be propelled by propelling the rod further through the blocked and punctured feed plunger in the direction of the front side of the cartridge.

Moreover, the invention can provide the device to comprise a blocking facility by which the feed plunger can be locked in the internal space of the container. Preferably, a limit stop can be used as a blocking facility in this context. Preferably, the limit stop is realized in that the internal space of the cartridge has a smaller diameter and/or cross-section than the internal space of the receptacle such that a step arises at the transition from the cartridge to the receptacle and serves as a blocking facility and/or as a limit stop for the motion of the feed plunger in the internal space of the receptacle in the direction of the front side of the tube-shaped container. Alternatively, the container, in particular the internal wall of the receptacle, is deformable by the blocking facility such that the feed plunger is clamped by the deformation or the deformation forms a limit stop. Theoretically, the blocking facility can just as well be a holding means secured to the rear side of the feed plunger in the direction of the external circumference of the feed plunger, such as a thread, a wire, or a pin, that is secured to the container on the rear side of the container or engages the container and thus tilts the feed plunger in the container such that it is canted and blocked.

Preferably, the feed plunger is arranged in the area of the rear side of the receptacle or in the rear side of the receptacle. Likewise, the dispensing plunger is preferably arranged on the rear side of the cartridge or in the area of the rear side of the cartridge.

In devices according to the invention, the tube-shaped container can be provided to have a one-part design, whereby the receptacle and the cartridge are preferably designed as a one-part thermoplastic resin body, whereby the container is particularly preferably manufactured using an injection molding process.

By this design, the tube-shaped container is inexpensive to manufacture and is particularly stable, including at the transition between the receptacle and the cartridge.

Moreover, the invention can provide the cross-sectional surface area of the internal space of the cartridge to be smaller than the cross-sectional surface area of the internal space of the receptacle.

What this attains, in particular, is that the highly viscous bone cement dough can still be extruded through a dispensing tube with a static mixer or a hose with a connected trocar by a manually driven extrusion device even if there is a downstream resistance in the flow direction of the cartridge. As a result, the device can be used for vertebroplasty even if manually driven extrusion devices are utilized. Moreover, the step thus produced can be used as a limit stop for the motion of the feed plunger in the direction of the front side of the tube-shaped container.

Preferably, the invention can also provide a securing means for securing an extrusion device to be arranged on the tube-shaped container, in particular on the rear side of the receptacle.

By this means, the extrusion device can be connected to the device according to the invention such as to be flush with it, and is affixable with respect to the device, and thus the monomer liquid can be evenly pushed into the cement powder and the cement dough can be evenly expelled from the cartridge.

A refinement of the present invention proposes to provide a limit stop on the inside of the container that limits the motion of the feed plunger in the direction of the front side, whereby the limit stop preferably limits the motion appropriately such that the feed plunger cannot be fully pressed out of the receptacle, whereby the limit stop is particularly preferably provided as a step arising from different shape or different cross-sections of the cylindrical internal space of the cartridge and the cylindrical internal space of the receptacle at the transition between the receptacle and the cartridge.

This structurally simple and inexpensive measure allows the position to be defined at which the feed plunger is reliably blocked.

In addition, it prevents the feed plunger, when the feed plunger is being propelled, from driving the dispensing plunger far forward in the cartridge or at least from driving the dispensing plunger sufficiently far forward such that the bone cement dough begins to flow out of the cartridge due to a joint motion of the dispensing plunger and feed plunger.

The limit stop limiting the motion of the feed plunger in the container in the direction of the front side of the container does not necessarily and not automatically mean that the feed plunger touches against the limit stop when it can no longer be driven further in the direction of the front side. This is the case because residues or fragments of the monomer liquid container, in particular fragments of a glass ampoule or of parts of the film of a film bag as monomer liquid container, may be jammed between the limit stop and the feed plunger and remain there without the function of the device being limited by this in any way or shape. The motion of the feed plunger in the direction of the front side of the container is blocked when the feed plunger reaches a position in which the limit stop limits its motion. Since the feed plunger is blocked, it can be punctured by the rod. Accordingly, the limit stop defines or limits the position of the feed plunger, in which the feed plunger is adapted to be punctured by the rod.

Preferably, the invention can provide the transition from the receptacle to the cartridge in the form of a limit stop for blocking the motion of the feed plunger in the direction of the front side of the container.

Moreover, the invention can provide the connection to be arranged in the dispensing plunger and/or to be arranged in the wall of the tube-shaped container, whereby the connection is preferably arranged in the dispensing plunger and connects a front side of the dispensing plunger to a rear side of the dispensing plunger that faces the monomer liquid container.

What this attains is that the monomer liquid can be guided and/or pushed into the cartridge easily and without great resistance. Moreover, there is then no need to provide further conduits in the wall of the tube-shaped container.

According to a preferred refinement, the invention can provide a filter, in particular a pore filter that is permeable to gases and the monomer liquid, but is impermeable to the cement powder, to be arranged at the site at which the connection merges into the internal space of the cartridge.

This prevents the cement powder from entering into the connection, from reacting there with the monomer liquid, and prevents the connection from becoming closed when the cement powder swells in the connection.

Preferably, the invention can provide the cement powder to touch against a front side of the dispensing plunger, in particular across the entire surface, whereby the cement powder is preferably pressed into the internal space of the cartridge.

This prevents any major gas inclusions from remaining in the cartridge, which would otherwise lead to gas inclusions in the bone cement dough when the monomer liquid is mixed with the cement powder. This cannot take place in the case of a tightly poured cement powder, since the monomer liquid wets the cement powder particles well and the surface tension of the monomer liquid then does not allow for any or at least any relevant gas inclusions to be present between the cement powder particles.

In this context, the invention can also provide the volume of the intervening spaces between the cement particles of the cement powder in the internal space of the cartridge to be in the range of 22% by volume to 40% by volume, relative to the total volume of the cement powder. The total volume of the cement powder preferably corresponds to the volume of the internal space of the cartridge that is limited by the dispensing plunger and by a closure in a dispensing opening on the front side of the cartridge.

A refinement of the present invention proposes the cartridge to comprise, on the front side, a dispensing opening that is closed by a closure, whereby the bone cement dough can be extruded from the cartridge through the dispensing opening, if the dispensing opening is open, and whereby the closure is permeable to gases and impermeable to the cement powder.

As a result, the cartridge is well-suited for use for storage of the cement powder. The closure is adapted to be opened. The internal space of the cartridge and the cement powder can be sterilized through the closure by evacuation and rinsing of the internal space of the cartridge with a sterilizing gas, such as ethylene oxide.

In this context, according to the invention, the closure is adapted to be pushed out of the dispensing opening by the propulsion of the dispensing plunger and the pressure of the bone cement dough applied onto the closure.

By this design, the cartridge opens automatically when the dispensing plunger is being driven.

Moreover, according to the invention, a dispensing tube and/or a flexible hose with a trocar is secured or securable to the front side of the cartridge, whereby the bone cement dough is extrudable through the dispensing tube and/or the flexible hose and the trocar, whereby a manually closable valve element, which is usable to control the flow of bone cement dough, is arranged on the dispensing tube or hose.

By this design, the device is well-suited for use for the application of bone cement dough in areas that are difficult to access or are exposed to X-rays. In particular, the device can thus be used as an applicator for vertebroplasty.

Moreover, the invention also proposes that the feed plunger is adapted to be punctured from a rear side by the rod comprising a tip or an edge, if the feed plunger is blocked from moving further in the direction of the front side of the tube-shaped container.

By this design, a more stable feed plunger can be used, since the pressure required for puncturing the feed plunger, at the same force, is increased due to the contact surface of the tip or of the edge being smaller. It is self-evident in this context that the tip or edge, for this purpose, is arranged on a front side of the rod that touches against the rear side of the feed plunger.

Preferred devices can be characterized in that the feed plunger is adapted to be punctured from the rear side by a rod with a force of at least 1 kN, if the feed plunger is blocked from moving further in the direction of the front side of the tube-shaped container.

It is assured by this design that the feed plunger is adapted to be punctured by the rod of a manually driven extrusion device.

The invention can also provide the feed plunger to comprise, on its rear side, a contact surface for the rod of the extrusion device and can provide the feed plunger to be manufactured from a plastic material, in particular to be manufactured from a thermoplastic resin.

By this design, the feed plunger can initially be driven stably and can later be punctured in the middle by the rod once the feed plunger is being blocked. As a result, the device is stable and safe to use. In this context, the invention can provide the contact surface in an axial top view to be at least of the same size as the cross-section of the rod.

Preferably, the invention can also provide the feed plunger to have a maximum thickness in the area of the contact surface of the rod of at most 4 mm, preferably of at most 3 mm, and particularly preferably of at most 2 mm.

This assures that the feed plunger can be punctured by a manually driven extrusion device, since the resistance of the material is reduced by the low thickness in the area to be punctured.

Moreover, the invention can provide the cross-section of the internal space of the cartridge to be at most 4 $cm^2$, preferably at most 2.5 $cm^2$, particularly preferably at most 1.2 $cm^2$.

Analogously, the invention can also provide the internal diameter of the cartridge to be less than 20 mm, preferably less than 15 mm, particularly preferably less than 11 mm.

Because of the small internal diameter, the cross-section of the internal space of the cartridge is sufficiently small such that the viscous bone cement dough can be extruded from the cartridge through the use of a manual extrusion device even if other conduits impeding the flow, such as a hose, a static mixer, or a trocar, are provided in the flow direction of the bone cement dough.

Moreover, the invention can provide the monomer liquid container to be a glass ampoule, a plastic ampoule, a plastic film bag, or an aluminium-plastic compound bag.

The monomer liquid can be stored in the device in these monomer liquid containers even over extended periods of time.

The invention can provide the volume of the monomer liquid in the monomer liquid container to be at least equal to the volume of the air-filled intervening spaces between the cement particles of the cement powder in the internal space of the cartridge.

The invention can also provide the volume of the monomer liquid in the monomer liquid container to be at least equal to the volume of the liquid conduits between the internal space of the cartridge and the internal space of the receptacle plus the volume of the air-filled intervening spaces between the cement powder particles in the cartridge.

By this design, it can be made sure that all of the cement powder can be wetted by the monomer liquid and that, thus, a homogeneous bone cement dough is produced.

According to a preferred refinement, the present invention can provide for at least one ventilation opening to be arranged in the wall of the receptacle, whereby the ventilation opening connects the internal space of the receptacle, in which the monomer liquid container is arranged, to the surroundings, whereby the at least one ventilation opening is preferably arranged sufficiently close to the feed plunger such that it is closed by a motion of the feed plunger in the direction of a front side of the receptacle before the monomer liquid container is opened through the motion of the feed plunger.

As a result, the internal space of the receptacle can be sterilized with a sterilizing gas. Concurrently, the monomer liquid cannot exit from the internal space of the receptacle, when the at least one ventilation opening is closed by the feed plunger moving in the direction of the front side of the receptacle and before the monomer liquid container is opened by the motion of the feed plunger, for example is squashed, splintered, or torn open by the feed plunger in the internal space of the receptacle.

To secure the functioning of the device according to the invention, the invention can provide a screen or a porous disk that is permeable to gases and liquids on a front side of the receptacle in the connection to the cartridge.

By this design, fragments or severed parts of the monomer liquid container can be prevented from getting into the cartridge and therefore into the bone cement. Moreover, said fragments or parts can also be prevented from impairing or blocking the liquid-permeable connection between the receptacle and the cartridge.

According to a preferred embodiment, the present invention can provide (1) a three-way valve, which is operable from outside, to be arranged in the flow direction of the bone cement dough, in a conduit downstream of the cartridge, and (2) a collecting container for reception of bone cement dough to be arranged on the three-way valve, whereby the conduit merges into an application opening that is arranged on the end of the conduit that faces away from the cartridge, whereby the three-way valve is designed appropriately such that it, being in a first position, provides a fluid connection between the application opening and the cartridge and closes a discharge channel toward the collecting container, and being in a second position, provides a fluid connection between the application opening and the collecting container and closes a passage to the cartridge.

What this attains when the extrusion process is interrupted is that the pressure acting on the bone cement in an extended dispensing opening, such as a hose, is removable by adjusting a three-way valve that is connected to the collecting container, the hose, and the cartridge, without any substantial amount of the bone cement dough continuing to flow. Simultaneously, this allows the pressure of the bone cement dough and of the starting components in the cartridge to be maintained all the way to the three-way valve and, in particular, in the mixer, if any is present. As a result the time that elapses between the three-way valve being opened and the bone cement dough exiting again is very short. Accordingly, the pressure of the cartridge is maintained between the three-way valve and the dispensing plunger, when the three-way valve is closed, whereas rapid pressure relief of the extended dispensing opening is attained between the three-way valve and the application opening since the bone cement dough flows off through the three-way valve in the closed position. The collecting container is provided to ensure that the bone cement dough does not contaminate the surroundings or the user, and prevents the bone cement dough from dripping out through the three-way valve. Theoretically, it may be sufficient to retain the bone cement dough. The collecting container can just as well be flexible and/or elastic and can expand when it takes up the bone cement dough exiting from the three-way valve.

The device thus contains an emergency relief valve in the form of the three-way valve by which the extrusion process can be stopped instantaneously once the bone cement dough starts to flow into undesired regions of the body, in particular of the vertebral body. Said emergency relief valve acts as a pressure relief for the extended dispensing opening of the device, in which the trailing pressure of the bone cement dough from the upstream regions is blocked and simultaneously the bone cement dough situated upstream of the emergency relief valve is relieved of pressure, by opening a channel that leads into the collecting container into which the bone cement dough can exit until the pressure in the hose and/or in the trocar is relieved.

Said storage and mixing devices can preferably be provided appropriately such that the collecting container is impermeable to the bone cement dough towards the outside, preferably in that the collecting container is liquid-tight or liquid-tight and gas-tight. The invention can also provide the collecting container to comprise a volume that is at least equal to half the volume of the extended dispensing opening, in particular of the hose and, if applicable, of the trocar, preferably at least equal to the volume of the extended dispensing opening, in particular of the hose and, if applicable, of the trocar.

The invention can provide a mixer for mixing of the bone cement, in particular a static mixer, between the cartridge and the extended dispensing opening or in the extended dispensing opening or between the cartridge and the three-way valve, whereby the three-way valve is preferred to be arranged between the mixer and the extended dispensing opening. In the latter case, the invention can provide the three-way valve, being in the first position, to provide a fluid connection between the application opening and the mixer and, being in the second position, to close the passage to the mixer.

Referring to devices according to the invention comprising a hose, the hose can preferably be flexible, at least regions thereof. The invention can also provide the extended dispensing opening to end in a connector having an internal thread, in particular in a Luer system adapter, or in a trocar.

Moreover, the invention can provide that the monomer liquid container can be opened in the inside of the receptacle through a motion of the feed plunger in the direction of a front side of the receptacle, preferably by breaking or tearing.

As a result, the monomer liquid container can be opened through the axial linear motion of the feed plunger. Accordingly, an extrusion device with only one rod as an axial linear drive can be used to open the monomer liquid container and to press the monomer liquid into the cartridge and also to extrude the bone cement dough from the cartridge.

The invention can also provide the feed plunger to comprise, on the rear-side face, a receptacle or a recess, in particular a cylindrical recess, for the rod of the extrusion device, in which a rubber cuff is preferably arranged as a sealing element or in which a plastic or metal disk as a sealing element that can be plastically deformed and punctured by the rod.

By this design, the monomer liquid can be prevented from leaking during the extrusion of the cement dough.

Moreover, the invention can provide the cartridge to be closed off on the front side by a cartridge head, whereby a dispensing opening is situated in the cartridge head and the dispensing opening is closed by a closure that is impermeable to the cement powder in the cartridge and is permeable to gas, in particular a pore filter, whereby the closure can preferably be opened through an axial pressure load or by action of a manual force.

Moreover, the invention can provide the cartridge to have a compressive strength of more than 10 bar, preferably of more than 50 bar, particularly preferably of more than 70 bar.

Moreover, the invention can provide an adapter for securing a hose or a trocar to be arranged on a dispensing tube or on a dispensing opening on the front side of the cartridge.

By this design, the device can be used for vertebroplasty.

In this context, the hose can be provided to have an internal diameter of less than 4 mm and a minimum compressive strength of 10 bar.

The objects underlying the present invention are also met by an extrusion device for propelling a feed plunger and a dispensing plunger of a device for mixing a bone cement dough from starting components and for dispensing the mixed bone cement dough, whereby the extrusion device comprises a bracket for securing the device and a rod that is adapted to be axially propelled with respect to the bracket, in which the rod comprises, on a front side, a hard tip or edge for puncturing the blocked feed plunger of the device, whereby a removable or piercable cap with a level front side is arranged on or is attached to the tip or edge.

The tip or edge can be blunt, flattened, or rounded in order to be able to adjust the pressure that is being applied by the edge or the tip, which needs to be at least sufficiently high, on the one hand, to be able to puncture the feed plunger of the device, and at the same time should not be too high such that the dispensing plunger is punctured or deformed to the extent that it jams in the cartridge.

In this context the invention can provide the extrusion device to be intended for propelling the feed plunger and the dispensing plunger and for puncturing the blocked feed plunger of a device according to the invention, whereby the device is preferably inserted into the extrusion device or is packaged jointly with the extrusion device in a packaging.

It is particularly advantageous to use the extrusion device according to the invention in conjunction with a device according to the invention.

Moreover, the invention can provide the extrusion device to comprise a lever that can be manually pivoted with respect to the bracket, whereby the rod can be manually propelled with the lever with the aid of a clamping facility, such as clamping jaws or clamping disks, whereby the clamping facility becomes firmly connected to the rod upon a motion of the lever in one direction and detaches from the rod upon a motion of the lever in the other direction such that the rod can only be moved in one direction by the lever.

By this design, the extrusion device can be held in one hand and the lever can be operated simultaneously with the same hand in order to drive the rod, whereby the propulsion of the rod can be used both for propelling a plunger, when the rod is used with the cap situated on the tip or edge of the rod, and for puncturing a plunger, when the rod is used without the cap.

The objects underlying the present invention are also met by a method for the production of a bone cement dough, in particular of a pasty PMMA bone cement dough, whereby the bone cement dough is produced from a cement powder and a monomer liquid through the use of a device, whereby the device comprises a tube-shaped container that forms, on its rear side, a receptacle with a cylindrical internal space, in which a monomer liquid container with the monomer liquid in it is arranged, and the container forms, on its front side, a cartridge with a cylindrical internal space that contains the cement powder, characterized by the following steps proceeding in the order given:

a) inserting the device in an extrusion device, whereby the extrusion device comprises a rod that can be propelled in an axial direction;

b) a feed plunger, supported such as to be mobile in the receptacle on the rear side thereof, is propelled in the direction of the cartridge by the rod, whereby the motion of the feed plunger opens the monomer liquid container and presses the monomer liquid from the receptacle into the cartridge, whereby the cement powder mixes with the monomer liquid in the internal space of the cartridge;

c) the motion of the feed plunger in the direction of the front side of the container is blocked;

d) the rod punctures the feed plunger and after puncturing the feed plunger hits on a dispensing plunger that is supported in the cartridge such as to be mobile; and e) the dispensing plunger is propelled in the direction of a front side of the cartridge by the rod, while the rod runs through the blocked and punctured feed plunger, whereby the mixture of cement powder and monomer liquid is expelled from the cartridge as bone cement dough due to the motion of the dispensing plunger.

It is preferred to secure the extrusion device to the receptacle of the device in step a).

The invention can also provide, in step b), the monomer liquid container to first be compressed between the feed plunger and the dispensing plunger before being opened.

The invention can also provide, in step b), the monomer liquid container to crack into fragments or to be torn open or cut open.

Moreover, the invention can provide, in step b) after the monomer liquid is pressed into the cartridge, the cement powder particles to swell in the monomer liquid and the radical polymerization of the monomer liquid to be triggered by reaction of the accelerator with the initiator.

The invention can also provide, in step e), the rod to run through the fragments, shreds, or residues of the monomer liquid container while the dispensing plunger is propelled by the rod.

In this context, the invention can provide the method to be implemented with a device according to the invention.

The method can be implemented particularly well with a device according to the invention.

Moreover, the invention can provide the method to be implemented with an extrusion device according to the invention.

The extrusion device according to the invention is particularly well-suited for implementing the method according to the invention.

Moreover, the invention can provide the rod to comprise, on a front side, a hard tip or edge for puncturing the blocked feed plunger of the device, whereby, in step a), a removable cap with a level front side is arranged on the tip or edge, and the cap is removed from the tip or edge after step c), and the rod is driven into the feed plunger by the tip or edge, whereby the device is preferably removed from the extrusion device earlier and the device is re-inserted into the extrusion device after removing the cap from the tip or edge.

By this design, the feed plunger can be propelled stably initially and later the feed plunger can be punctured by the tip or edge of the rod without requiring too much force.

According to a preferred refinement, the method according to the invention can provide a closure, in particular a pore filter, to be moved in or pushed out of a dispensing opening on the front side of the cartridge before step c) or in step c) by the pressure acting on the mixture of cement powder and monomer liquid, whereby the closure is then preferably removed from the dispensing opening and an extended dispensing tube or a hose with a trocar is secured to the front side of the cartridge and/or the cap is removed from the tip or edge of the rod.

By this design, the emerging closure allows the user to recognize that the device is ready for use and that the bone cement dough can be extruded from the device.

Preferably, the invention can also provide the crushed or slit-open or burst-open monomer liquid container to be pushed together in step b) and simultaneously gas to be pushed from the receptacle through a connection into the cartridge and to be pushed through the cement powder in the cartridge to the outside, and whereby, in step d), the rod driven through the feed plunger displaces the fragments of the monomer liquid container.

What this attains is that the residues of the monomer liquid container are pushed together in the area of the receptacle that is pushed together by the feed plunger, and that most of the monomer liquid is pressed from the receptacle into the cartridge.

The invention can provide, in step e), a gas-permeable and powder-impermeable closure to be pushed out of a dispensing opening on the front side of the cartridge by the pressure of the preceding bone cement dough or the closure to be removed manually.

By this design, the user sees that the device is ready for application of the bone cement dough.

Lastly, the invention can provide, in step d) right before the application of the bone cement dough, a trocar with a hose to be connected to the cartridge on the front side of the cartridge on a dispensing opening and the bone cement dough subsequently to be extruded through the hose and the trocar and, if applicable, a dispensing tube due to the forward motion of the dispensing plunger by further actuation of the extrusion device.

This allows the bone cement dough to also be applied in regions that are difficult to access, such as, for example, in the area of vertebral bodies, and in areas exposed to X-rays.

The invention is based on the surprising finding that providing a feed plunger that is initially mobile and subsequently blocked such that it can be punctured by a rod of an extrusion device allows the rod to be used initially for driving the feed plunger in order to open the monomer liquid container and to transfer the monomer liquid into the cement powder, and subsequently to use the same rod for driving a dispensing plunger arranged in series downstream in order to extrude the bone cement dough from the cartridge. For puncturing of the feed plunger, firstly, a cap with a level front side can be removed from a tipped or edged front side of the rod or—which is equivalent—a cap with a tip or an edge can be attached to the rod with a level front side in order to puncture the feed plunger with it, or secondly, the tip of the rod itself can be well-suited for puncturing and for driving the feed plunger. In the latter case, the feed plunger needs to be sufficiently stable and/or sufficiently smooth-running in order to use the feed plunger initially for opening and, if applicable, crushing the monomer liquid container and for pressing the monomer liquid from the receptacle into the cartridge, and concurrently it needs to be sufficiently unstable and/or susceptible to puncturing in order to be able to puncture the feed plunger by the front side of the rod, if the movement of the feed plunger is blocked. For this purpose, film bags are preferred as monomer liquid containers, since they provide less resistance to the motion of the feed plunger than the fragments of crushed glass ampoules.

The use of a dispensing plunger that is separate and independent of the feed plunger allows a cartridge to be used as well that has a particularly small internal space that is smaller than the receptacle for the common and broader monomer liquid containers. By this design, it is still feasible to extrude the viscous or highly viscous bone cement dough from the thin internal space of the cartridge against the resistance of a hose, and to apply it. As a result, the device and the method can also be used for vertebroplasty.

Among the essential advantages of the device according to the invention are that the two starting components of the bone cement, in particular of the spine cement, are stored in the closed cementing system and that the starting components are mixed in the closed device. This assures that the user does not need to fill the device. This concerns a full-prepacked cementing system. The medical user is not at all exposed to the individual starting components of the spine cements and/or bone cements. As a result, the unpleasant odor is minimized. It is a particular advantage of the device that the monomer liquid is pressed into the cement powder by simply moving forward a rod of a manually driven extrusion device. In the process, the air present between the cement powder particles is displaced by the monomer liquid. A homogeneous bone cement dough is produced without any need for any manual mixing with mixing rods with mixing vanes. This assures that the error-prone manual mixing is no longer required. The operation of the device is maximally simplified. This concerns a ready-to-use system.

The augmentation of fractured vertebral bodies always takes place under permanent fluoroscopy (X-ray monitoring). It is another advantage of the device that, due to the cross-section of the cartridge being small, the extrusion pressure on the cement dough upon actuation of the manually driven extrusion device is so high that the cement dough can be pressed through 20 cm of a pressure-resistant hose at an internal diameter of 3 mm. Due to the hose being 20 cm in length, the hands of the radiologist and/or orthopaedist are outside the area exposed to X-rays. This significantly reduces the radiation exposure of the physicians.

With an appropriate design of the device and/or suitable process steps, a manually driven extrusion device can be used. Moreover, with suitable measures according to the invention, no monomer liquid and no bone cement dough leaks from the device or contaminates the environment during storage and mixing of the bone cement dough.

The particular advantage of the device according to the invention is that manually driven extrusion devices can be used to extrude a two-component spine cement and/or the bone cement dough for vertebroplasty through a thin hose into the trocar. The augmentation of vertebral bodies takes place under permanent X-ray control. Having a hose between the trocar and the applicator allows the physician to not have to work with his or her hands within the range of the X-rays. No complex expensive hydraulic application devices are required in this context.

The device can be used as a hygienic disposable product since it can be manufactured largely from plastics and since all parts including the internal spaces and the cement powder can be sterilized with ethylene oxide.

An exemplary device according to the invention for storage, mixing, and dispensing of PMMA bone cement for augmentation of vertebral bodies can, for example, comprise:

a) a one-part tube-shaped body that is sub-divided into a hollow cylinder-shaped cartridge section (of the cartridge) and a hollow cylinder-shaped cartridge section (of the receptacle), whereby the internal diameter of the hollow cylinder-shaped cartridge is smaller than the internal diameter of the hollow cylinder-shaped receptacle, and whereby a connecting element for connection to an extrusion device is attached on the end of the receptacle;

b) a monomer liquid container in the receptacle;

c) a feed plunger that is impermeable to liquids and gases and is axially mobile in the hollow space of the receptacle;

d) cement powder that is arranged in the cartridge;

e) a dispensing plunger that is axially mobile in the hollow space of the cartridge and forms a boundary for the cement powder in the direction of the receptacle, whereby the dispensing plunger possesses at least one feedthrough that is permeable to gases and liquids, but is impermeable to powder particles, and connects the front side to the rear side of the dispensing plunger;

f) a cartridge head that forms a boundary for the cement powder in the cartridge, whereby the cartridge head contains a feedthrough as dispensing opening that is connected to a dispensing tube;

g) a closure plunger that is permeable to gases and liquids and reversibly closes the feedthrough of the cartridge head; and h) whereby the feed plunger is punctured by a rod (which can also be called a pestle) of an extrusion device by the action of a force of more than 1 kN.

The device can be used as a hygienic disposable product since it can be manufactured largely from plastics and since all parts including the internal spaces and the cement powder can be sterilized with ethylene oxide.

A method according to the invention can be implemented, for example, with the exemplary device for mixing of the cement powder and the monomer liquid while forming bone cement dough, comprising the following consecutive steps:

a) connecting the extrusion device to the connecting element of the receptacle of the cartridge;

b) propelling the rod of the extrusion device;

c) shifting the dispensing plunger in the direction of the cartridge head;

d) compressing the at least one monomer liquid container between the dispensing plunger and the feed plunger;

e) bursting or tearing the monomer liquid container;

f) pushing together the burst or torn monomer liquid container and pressing out the air from the internal space of the receptacle and the monomer liquid with the feed plunger through the at least one opening of the dispensing plunger into the cement powder into the internal space of the cartridge;

g) spreading of the monomer liquid in the cement powder while simultaneously displacing the air from the intervening spaces of the cement powder particles;

h) wetting of the cement powder particles by the monomer liquid;

i) allowing air to escape from the cement powder through the gas-permeable closure plunger;

j) swelling of the cement powder particles due to the monomer liquid and triggering of the radical polymerization of the monomer liquid through reaction of the accelerator with the initiator;

k) forming of the bone cement dough from the cement powder and the monomer liquid;

l) taking the extrusion device off the cartridge;

m) removing a cup and/or a plugged-on cap from the rod made of metal of the extrusion device;

n) if applicable, reconnecting the extrusion device to the receptacle;

o) moving the metal rod further in the direction of the cartridge head;

p) puncturing the feed plunger at the contact surface using the rod;

q) displacing the burst monomer liquid container by the metal rod;

r) moving the dispensing plunger in the direction of the cartridge head using the metal rod, whereby the metal rod moves through the punctured feed plunger and the residues of the burst monomer liquid container;

s) expelling the closure plunger or manually removing the closure plunger;

t) connecting an adapter of the dispensing tube to a trocar or to a hose; and u) extruding the bone cement dough through the dispensing tube due to the forward motion of the dispensing plunger by the actuation of the extrusion device.

BRIEF DESCRIPTION OF THE DRAWING

Further exemplary embodiments of the invention shall be illustrated in the following detailed description on the basis of fourteen schematic figures, though without limiting the scope of the invention. In the figures:

FIG. 5 includes FIGS. 5A, 5B, and 5C which show three schematic perspective views of inventive devices according to FIGS. 1 to 4 with different connectors on the cartridge head;

DETAILED DESCRIPTION OF THE INVENTION

For purposes of simplification, the same reference numbers are used for some identical components in the figures even if the embodiments are different.

Figure 11:
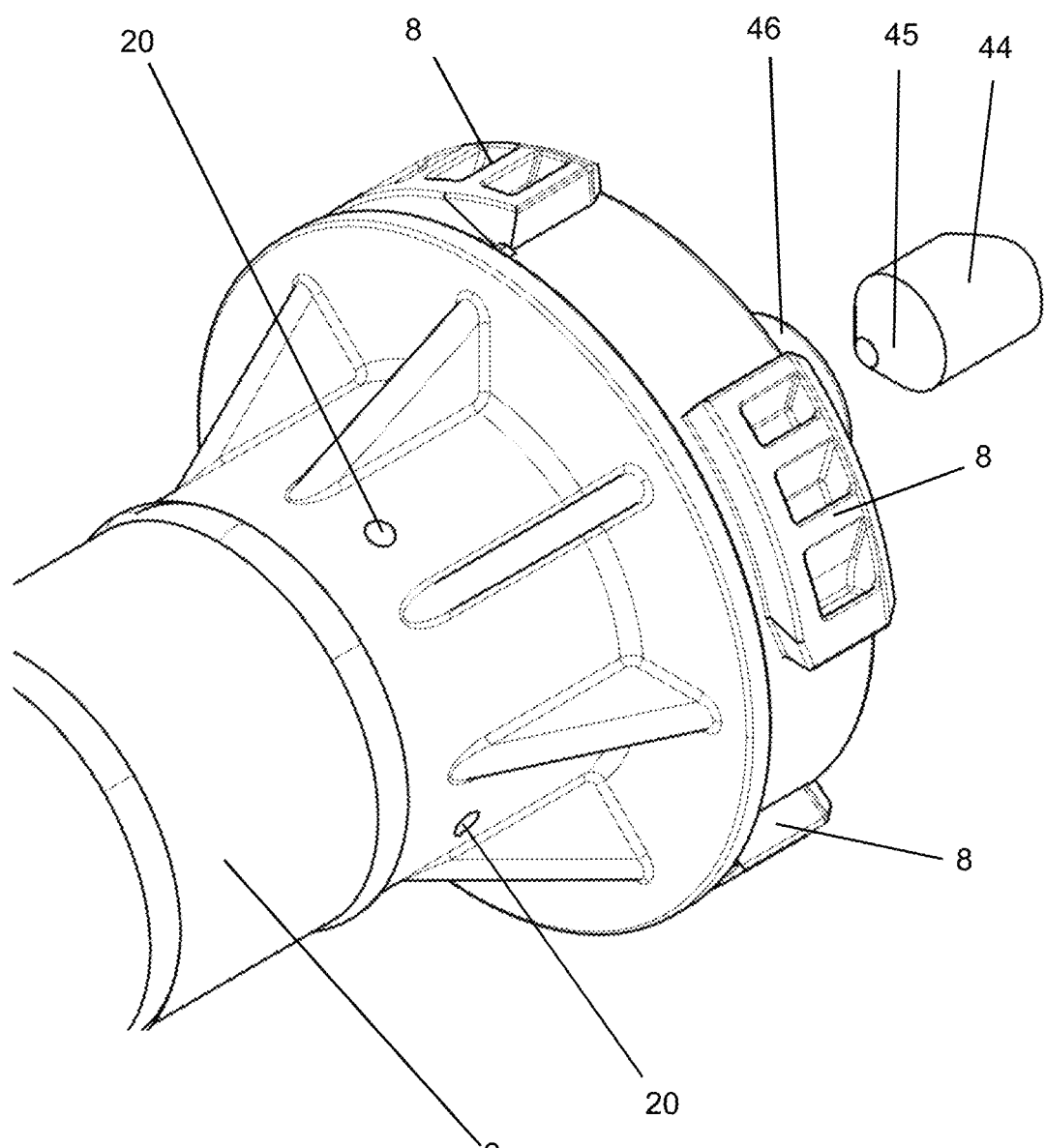
FIG. 11 shows a schematic perspective partial view as a detail view of the rear-side part of the device according to FIGS. 1 to 10 before insertion into the extrusion device.

FIGS. 1 to 11 show depictions of a first device according to the invention. FIGS. 1 to 3 and 5 show various schematic views of a first exemplary device according to the invention. FIGS. 4 and 6 to 10 show schematic cross-sectional views as detail views through various regions of the device according to the invention, and FIG. 11 shows a perspective partial view of a rear side of the device.

The device according to the invention essentially consists of a tube-shaped container made of plastics that forms, as a front part (on the top in FIGS. 1 and 2, on the left in FIGS. 3, 4, 6, 9, and 10, and on the top right in FIG. 5) a cartridge 1 with a cylindrical internal space and forms, as a rear part, a receptacle 2 for a glass ampoule 3 (or plastic ampoule 3). The rear side of the device is shown on the bottom in FIGS. 1 and 2, on the right in the depictions of FIG. 3, and on the bottom left in FIG. 5, and in FIGS. 8 and 11. The tube shape can be seen particularly well in the cross-sectional views of FIGS. 1 and 3. Both the internal space of the cartridge 1 and the internal space of the receptacle 2 are cylindrical and have a circular footprint. In this context, the diameter of the internal space of the cartridge 1 is smaller than the diameter of the internal space of the receptacle 2. The container with the receptacle 2 and the cartridge 1 is preferably manufactured from plastics with the aid of an injection molding technique. Accordingly, the receptacle 2 also comprises a cylindrical internal space into which the glass ampoule 3 is plugged. A monomer liquid 4 is situated in the glass ampoule 3. A cement powder 5 is filled or, preferably, pressed into the internal space of the cartridge 1. The monomer liquid 4 and the cement powder 5 are the starting components 4, 5 of a PMMA bone cement that can be produced with the device. Due to the glass ampoule 3, the monomer liquid 4 can be stored in the receptacle 2 and therefore in the device for very long times. The cement powder 5 can also be stored in the device over extended periods of time. The device is therefore well-suited for storing the monomer liquid 4 and the cement powder 5 as starting components of a bone cement dough of the PMMA bone cement. But the device is also well-suited and intended for mixing of the bone cement dough from the starting components and for dispensing the mixed bone cement dough.

A feed plunger 6 made of plastics that is mobile in a longitudinal direction in the cylindrical internal space of the receptacle 2 is arranged in the receptacle 2. The feed plunger 6 is arranged in the area of a rear side of the receptacle 2. The glass ampoule 3 can be compressed and thereby cracked in the receptacle 2 by the feed plunger 6 by pushing the feed plunger 6 in the direction of the front side, i.e., in the direction of the cartridge 1. The feed plunger 6 comprises, on its front side, wipers by which fragments of the glass ampoule 3 can be wiped off the internal wall of the receptacle 2.

A dispensing plunger 7 made of plastics is arranged in a rear side (on the bottom in FIGS. 1 and 2, on the right in FIGS. 3 and 9) of the internal space of the cartridge 1. A securing means 8 is provided on the rear side of the receptacle 2 and can be used to connect the receptacle 2 to an extrusion device 43 (not shown in FIG. 1, but see FIGS. 3 and 8). The securing means 8 is preferably well-suited and intended for the formation of a bayonet lock 8. By this means, the feed plunger 6, which is freely accessible from the rear side of the receptacle 2, can be propelled in the direction of the front side by the extrusion device 43.

The feed plunger 6 is shaped like a short tube that is closed off by a planar wall on its front side that faces the glass ampoule 3. The wall comprises, in the middle, a predetermined breakage site 9 that is accessible from the rear, i.e., from a rear side of the feed plunger 6 through a recess 10. The stabilization and sealing of the remaining feed plunger 6 is attained by a tube-shaped sleeve 12 that is also manufactured from plastics and is preferably provided in the form of a rubber cuff 12. Accordingly, the thickness of the material of the feed plunger 6 is reduced in the area of the predetermined breakage site 9.

The cartridge 1 and the receptacle 2 have a one-part design in the form of a joint injection molded part. The receptacle 2 and the cartridge 1 are connected to each other in liquid-permeable manner with respect to the monomer liquid 4 by a feedthrough 14 in the dispensing plunger 7. The feedthrough 14 through the dispensing plunger 7 merges through a pore filter 16, which is impermeable to the cement powder 5, but permeable to the monomer liquid 4, into the internal space of the cartridge 1.

A filter 18, by which the fragments of the glass ampoule 3 can be retained, is arranged in the connection to the feedthrough 14 in the tube-shaped container. Instead of the filter 18 or in addition to the filter 18, a screen can be provided just as well or also. The filter 18 is arranged in the dispensing plunger 7.

The wall of the receptacle 2 is provided with multiple ventilation openings 20 through which the internal space of the receptacle 2 can be sterilized with the aid of a sterilizing gas such as ethylene oxide. Said ventilation openings 20 are not shown in FIGS. 1 and 3, but are shown and labelled in FIGS. 2, 5, and 11. The ventilation openings 20 are arranged immediately adjacent to the feed plunger 6 such that the feed plunger 6 immediately closes the ventilation openings 20 when it is being propelled in the direction of the cartridge 1. This prevents monomer liquid 4 from exiting through the ventilation openings 20 when the glass ampoule 3 in the receptacle 2 is opened.

The cylindrical feed plunger 6 has an external circumference that matches the cylindrical geometry of the internal space of the receptacle 2 and is sealed by two circumferential seals 26 in a liquid-tight manner with respect to the internal wall of the receptacle 2. Likewise, the dispensing plunger 7 is sealed in a liquid-tight manner with respect to the internal wall of the cartridge 1 by two circumferential seals 28. The purpose of said seals 26, 28 is to prevent monomer liquid 4 or bone cement from exiting in order to prevent contamination of the surroundings (the OR theater and the user). For this purpose, the seals 26, 28 can consist of rubber.

The front side of the cartridge 1 merges into a dispensing tube 34 that comprises an external thread. A pore filter 36 that is impermeable to the cement powder 5, but is permeable to gases, is arranged on the inside of the dispensing tube 34. A cap 38 is secured to the external thread of the dispensing tube 34, whereby the front part of the cap 38 is filled with a Styrofoam or foam 40. Two wings 42 are provided on the cap 38 such that the cap 38 can be unscrewed conveniently from the dispensing tube 34 in the way of a wing screw. The cap 38 comprises lateral openings 39. Due to this design, the inside of the cartridge 1 and the cement powder 5 can be sterilized with the aid of ethylene oxide, since the openings 39 in the cap 38, the Styrofoam or foam 40, the pore filter 36, and the intervening spaces between the powder particles of the cement powder 5 are permeable to air. Concurrently, air can be pressed out of the receptacle 2 through the cement powder 5, the pore filter 36, the Styrofoam or foam 40, and the openings 39 in the cap 38, when the feed plunger 6 is pressed in the direction of the receptacle 2

The cement powder 5 is enclosed in the cartridge 1, since all openings 39 and feedthroughs 14 are closed with the aid of the pore filters 16, 36 such as to be impermeable to the cement powder 5. The content of the cartridge 1 can be sterilized by evacuation and rinsing with ethylene oxide in this context. By this design, the device is also well-suited for long-term storage of the cement powder 5.

Figure 1:
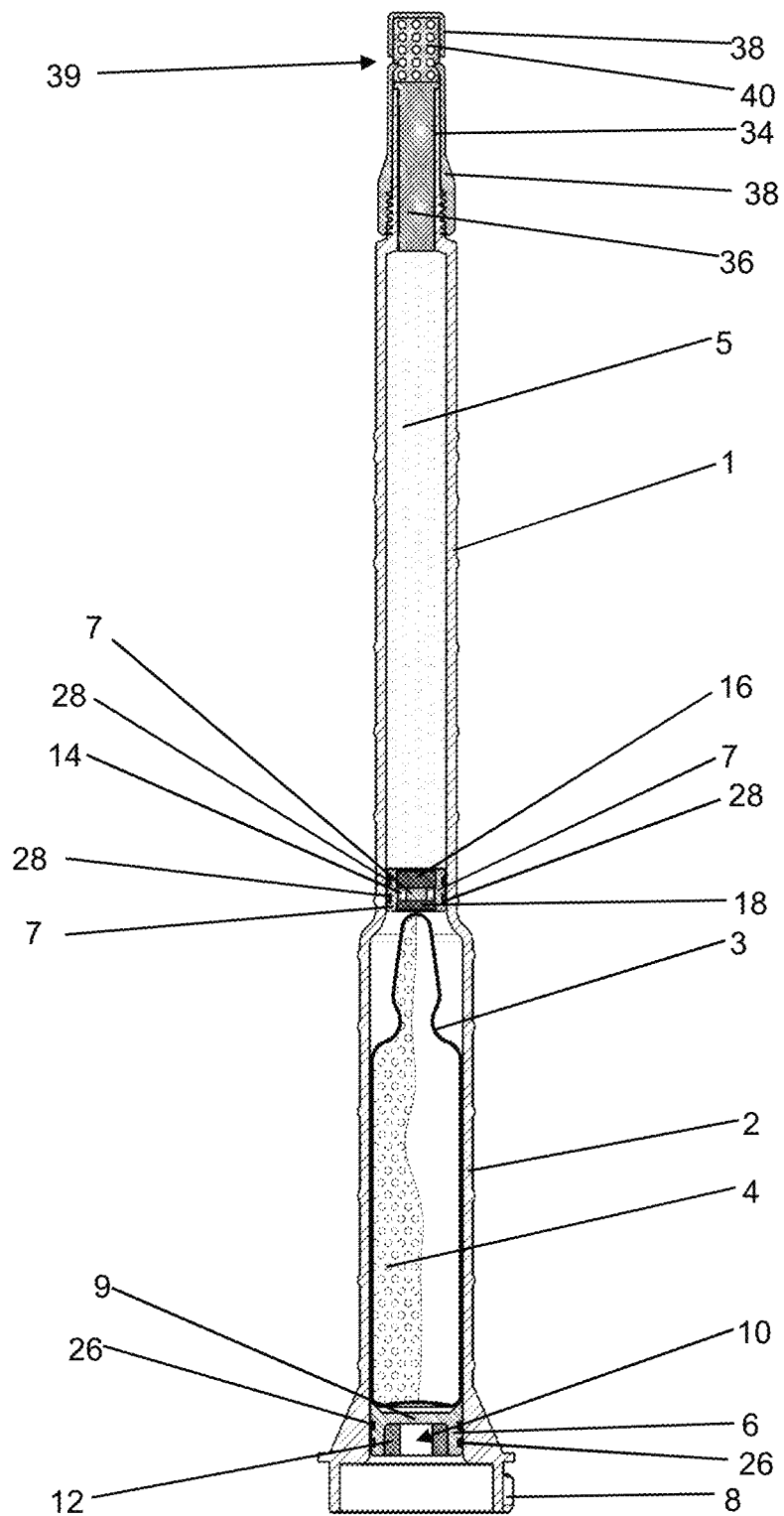
FIG. 1 shows a schematic cross-sectional view of an exemplary device according to the invention for storage and mixing of a monomer liquid and a cement powder.
Figure 2:
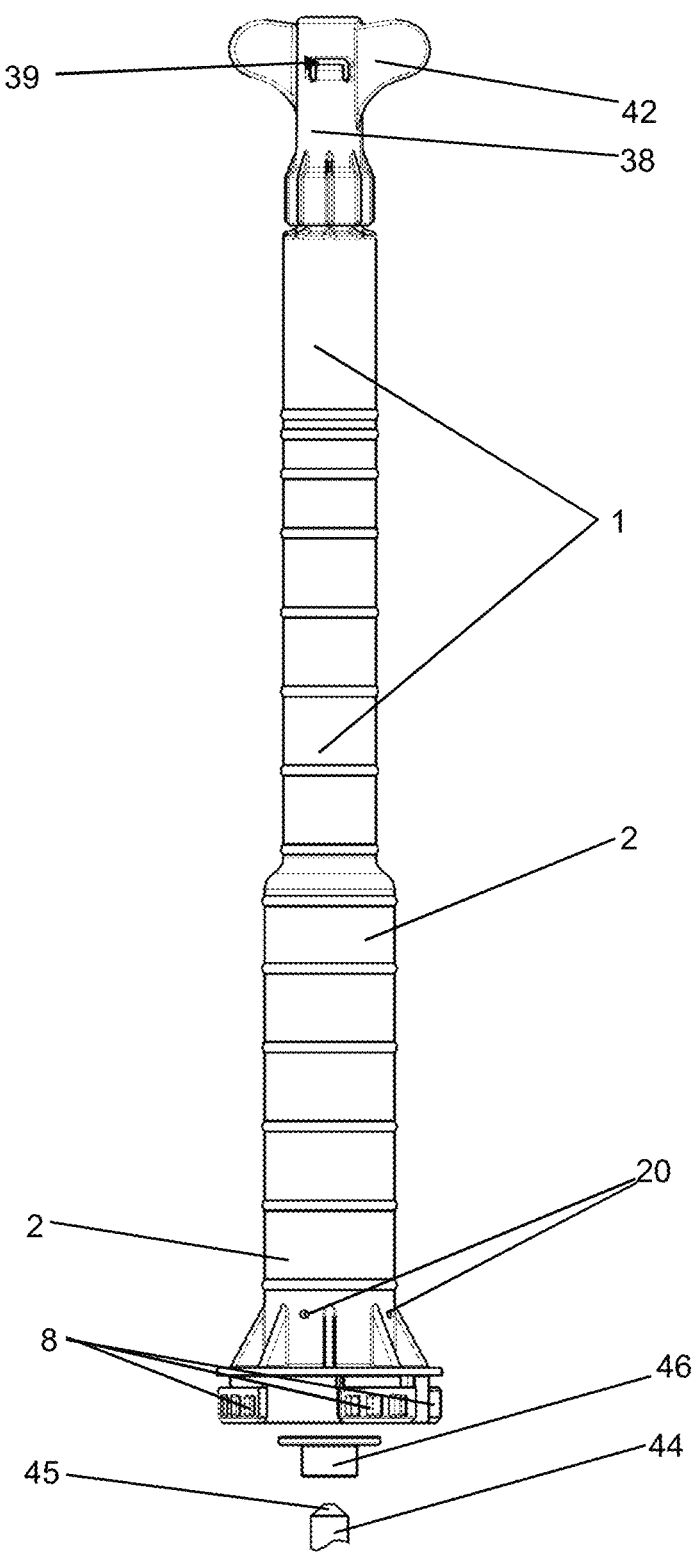
FIG. 2 shows a schematic side view of the device according to FIG. 1.
Figure 3A:
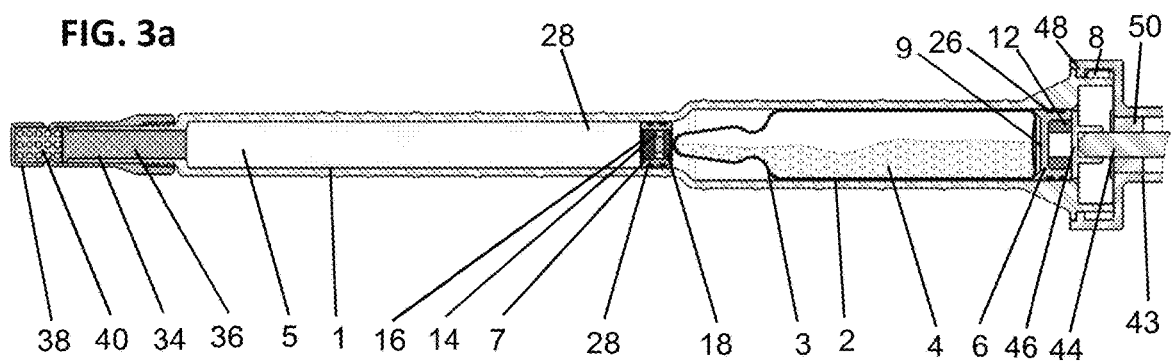
FIG. 3 includes FIGS. 3A, 3B, 3C, and 3D which show four schematic cross-sectional views of the device according to FIGS. 1 and 2 with a connected extrusion device according to the invention one over the other in order to illustrate the procedure of the method according to the invention.
Figure 3B:
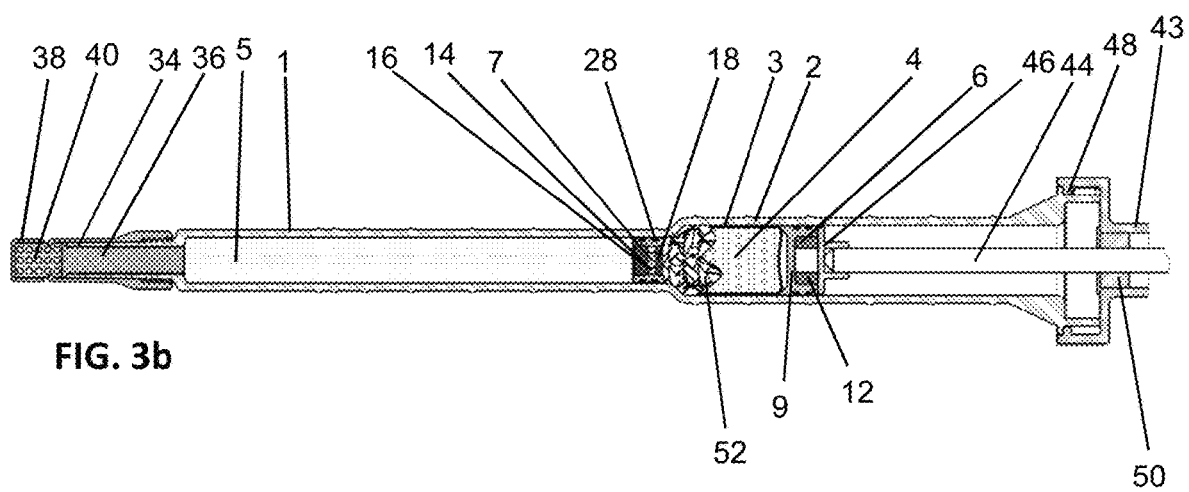

FIG. 3 shows four schematic cross-sectional views (namely, FIGS. 3A, 3B, 3C, and 3D) of the device according to FIGS. 1 and 2 on top of each other for illustration of the procedure of a method according to the invention. At the outset of the method, the device is in the starting state that is also shown in FIG. 1. Being in this state, the device is inserted into the extrusion device 43 according to the invention, which largely corresponds to a conventional cartridge gun. The extrusion device 43 comprises a rod 44 that can be propelled linearly. Only the front part of the extrusion device 43, which differs from conventional extrusion devices, is shown. The extrusion device 43 also comprises a handle and a tilting lever (not shown in FIG. 3) for manually driving the rod 44 of the extrusion device 43, like conventional manually driven extrusion devices. The device is secured to the extrusion device 43 by the securing means 8 (see FIG. 3A and FIG. 8). The rod 44 ends, on its front side, in a tip 45, which is initially covered by a removable cap 46. The rod 44 pushes, by means of the cap 46, onto the sleeve 12 and/or rubber cuff 12 of the feed plunger 6, when the extrusion device 43 pushes the rod 44 into the receptacle 2. For this purpose, the extrusion device 43 is connected to the rear side of the receptacle 2 through an opposite securing means 48 such that the cap 46 pushes onto the feed plunger 6 and propels it in the direction of the cartridge 1 when the rod 44 is propelled forward. For this purpose, the rod 44 is supported such as to be linearly mobile with respect to a bearing 50 and, through it, with respect to the opposite securing means 48 and therefore with respect to the receptacle 2.

Operating the extrusion device 43 propels the rod 44 and, through the rod 44, the feed plunger 6 in the direction of the cartridge 1. Since the glass ampoule 3 touches against the dispensing plunger 7 on its front side, the internal space of the receptacle 2 decreases in size and the glass ampoule 3 fractures and the monomer liquid 4 exits from the glass ampoule 3 into the internal space of the receptacle 2. The dispensing plunger 7 cannot be pushed in the direction of the pore filter 36 by the glass ampoule 3 when the cement powder 5 is dry, i.e., not wetted by the monomer liquid 4, since the dry cement powder 5 does not flow and blocks any motion of the dispensing plunger 7. The situation is shown in FIG. 3B and in a magnified detail view in FIG. 8. Supernatant air from the receptacle 2 is pushed through the filter 18, the feedthrough 14, the pore filter 16, through the intervening spaces between the particles of the cement powder 5, through the pore filter 36, through the foam 40, and out of the openings 39 in the cap 38 out of the device.

Figure 4:
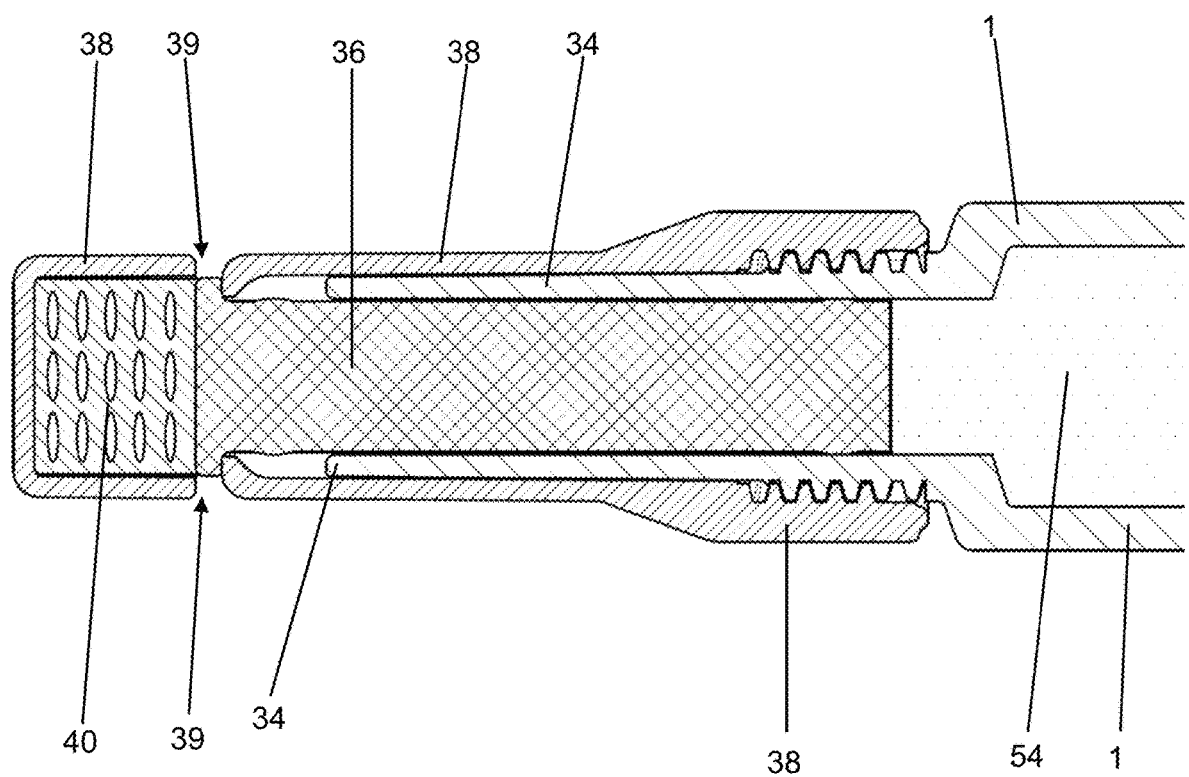
FIG. 4 shows a schematic cross-sectional view through the front part of the inventive device according to FIGS. 1 to 3 with a pore filter pushed forward.

Lastly, only small fragments 52 of the glass ampoule 3 remain and are retained by the filter 18 and remain in the tube-shaped container. The monomer liquid 4 is pressed through the filter 18, the feedthrough 14, and the pore filter 16 into the cement powder 5 and there starts to react with the cement powder 5 such that the bone cement dough 54 is produced from the mixture 54. This situation is shown in FIG. 3C and as a detail view in FIG. 9. As soon as the mixture 54 is produced, the pore filter 36 is driven forward by the pressure acting on the mixture 54 due to the pressure acting on the dispensing plunger 7, and compresses the foam 40. When the pore filter 36 slides forward, it becomes visible to the user from the outside through the opening 39 in the cap 38. This situation is shown in FIG. 4. For this purpose, the pore filter 36 preferably differs in color and brightness from the foam 40. For example, the foam 40 can be white and the pore filter 36 can be red.

Being in this state, the device is removed from the extrusion device 43 and the cap 46 is removed from the tip 45 of the rod 44. Alternatively, the tip 45 of the rod 44 can just as well be driven through the feed plunger 6 at a force that is sufficient for this purpose. In addition, the cap 38 with the pore filter 36 and the foam 40 is unscrewed and, instead, an extended dispensing opening is screwed onto the dispensing tube 34 (also refer to FIG. 5). Subsequently, the device with the extended dispensing opening is secured again to the extrusion device 43 by the securing means 8.

Figure 6:
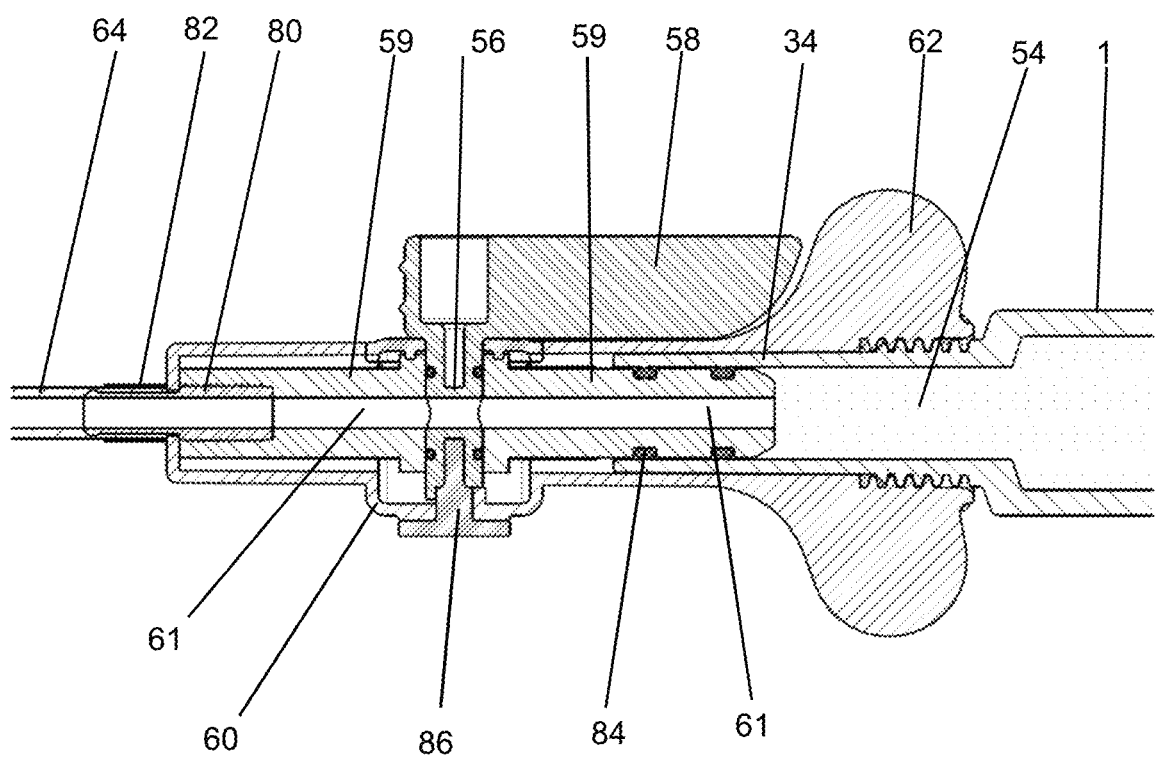
FIG. 6 shows a schematic cross-sectional view as a detail view of a three-way valve for an extended dispensing opening according to FIG. 3D.
Figure 7:
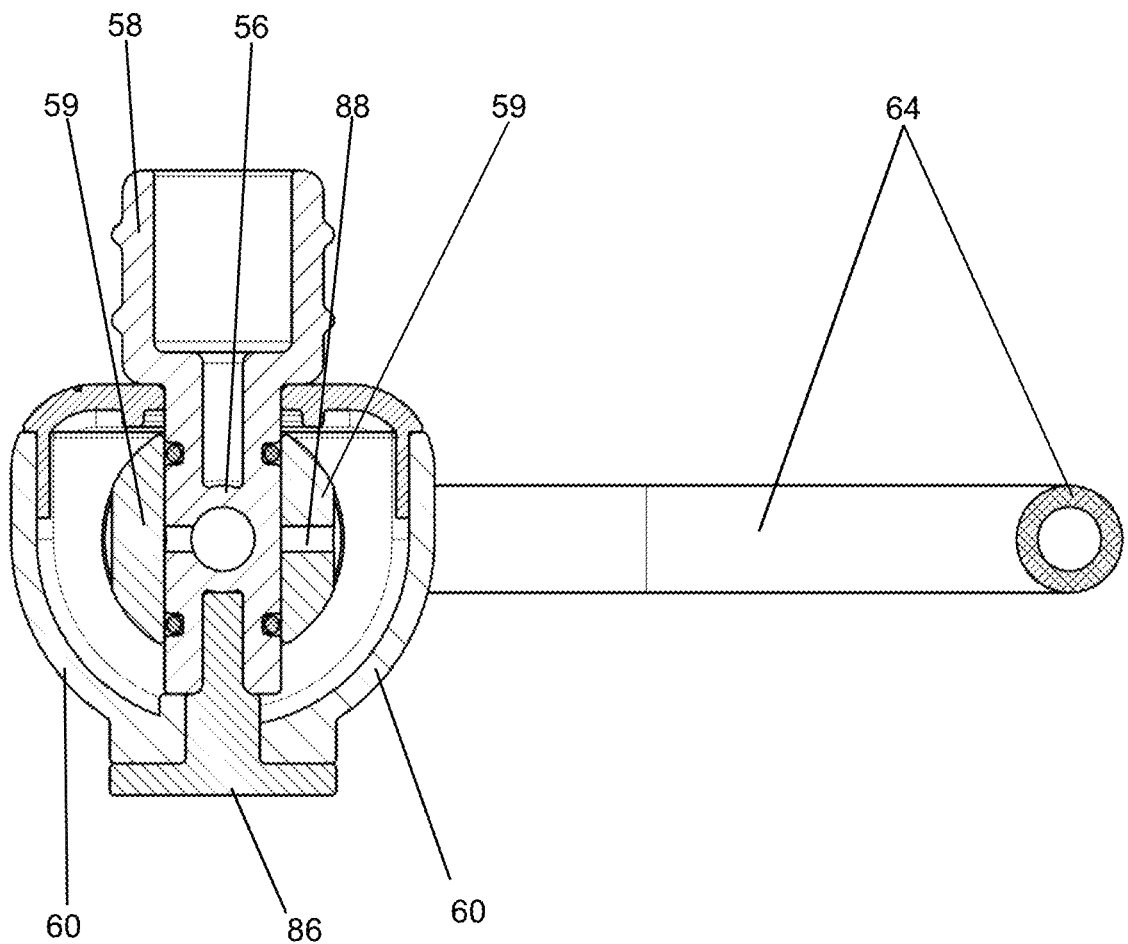
FIG. 7 shows a schematic cross-sectional view as a detail view of the three-way valve according to FIG. 6 with a sectional plane perpendicular to the flow direction of the bone cement dough.
Figure 8:
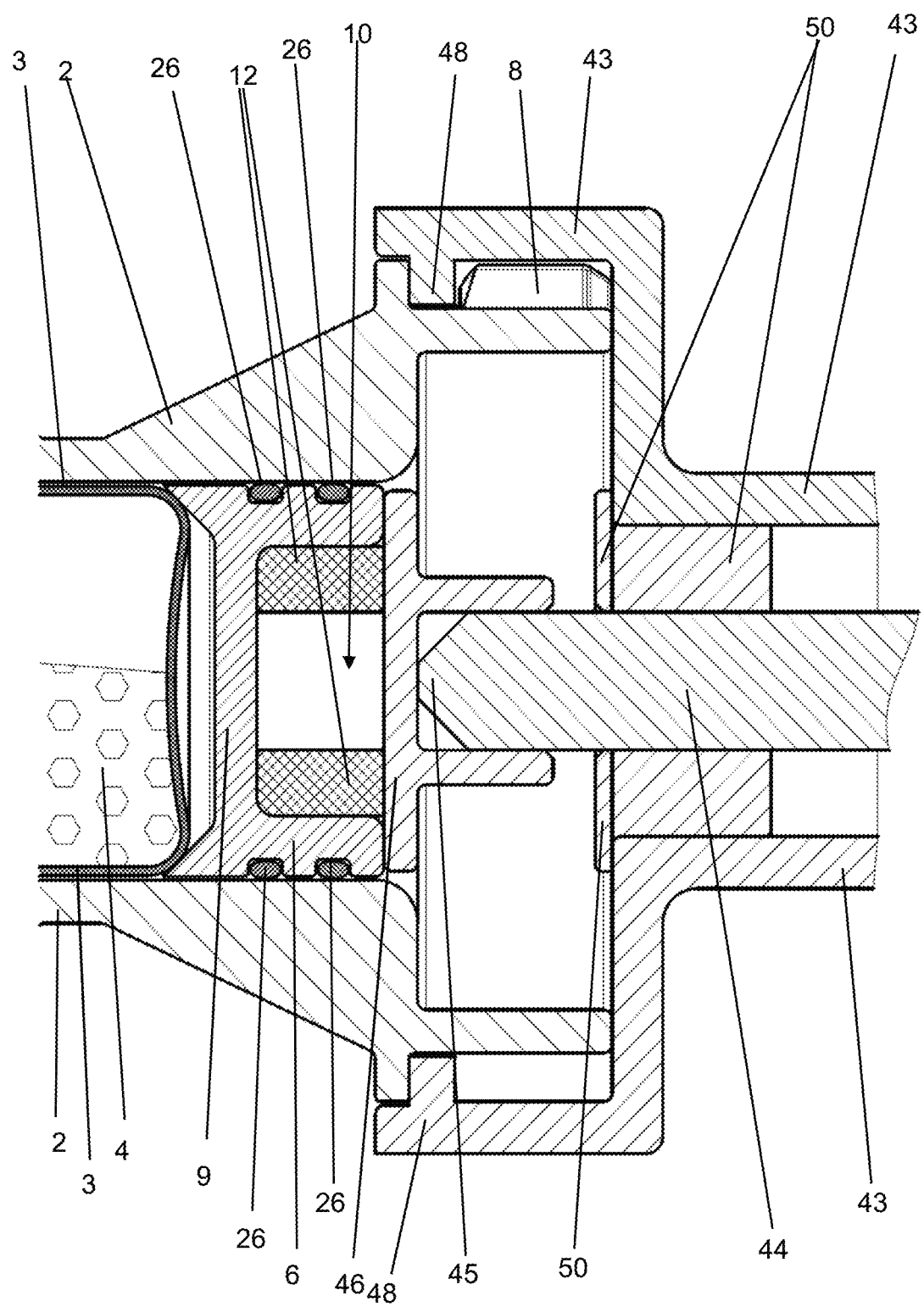
FIG. 8 shows a schematic cross-sectional view as a detail view of the connection of the device according to FIGS. 1 to 7 with an extrusion device according to the invention.
Figure 9:
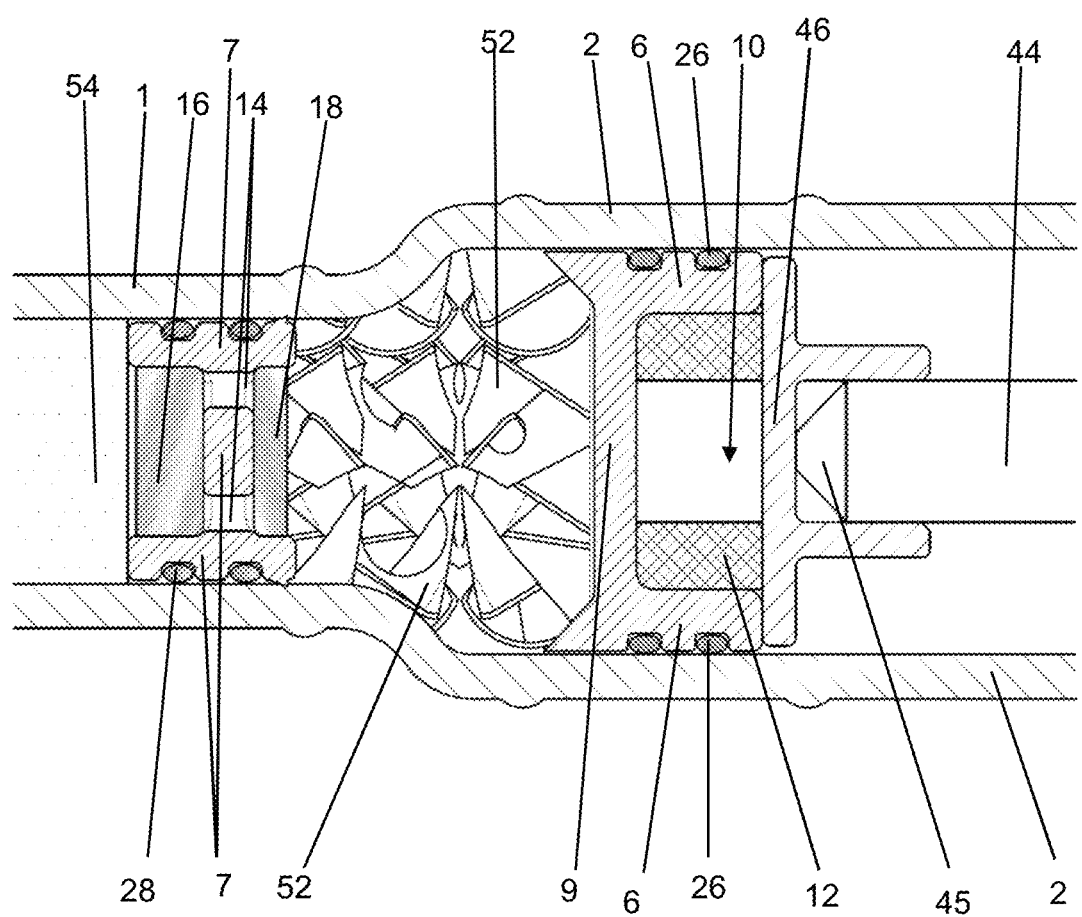
FIG. 9 shows a schematic cross-sectional view as a detail view of the transition from the receptacle to the cartridge before dispensation of the bone cement dough.
Figure 10:
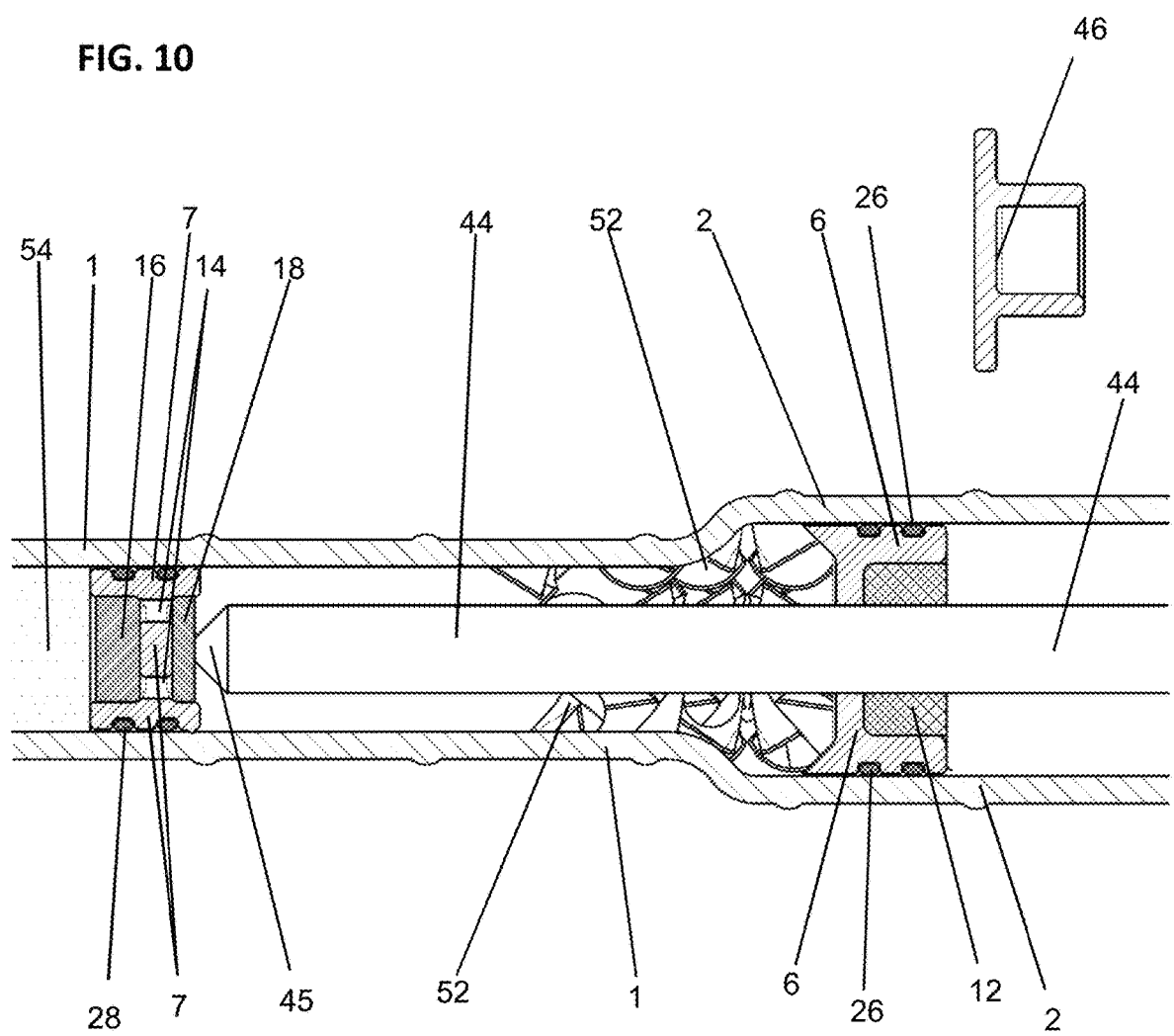
FIG. 10 shows a schematic cross-sectional view as a detail view of the middle part of the device according to FIGS. 1 to 9 during the extrusion of the bone cement dough.

The extended dispensing opening comprises a valve system with a three-way valve 56 that can be operated manually from outside through a T-handle 58. The three-way valve 56 is seated in a tight fit in a tube 59 that forms the valve seat 59. FIGS. 6 and 7 show schematic cross-sectional views as detail views through a valve system that can be used as part of the inventive device according to FIGS. 1 to 5. A collecting container 60, which is closed with respect to the outside and serves for receiving bone cement dough 54, is arranged in the area of the three-way valve 56. A passage 61 forming the inside of the tube 59 is provided in the tube 59. The passage 61 in the front side of the tube 59 is connected to the receptacle 60 via the three-way valve 56 such that pressurized bone cement dough 54 can divert from the front side of the extended dispensing opening to this location such that no more than a small amount of the bone cement dough 54 continues to flow from the extended dispensing opening when the three-way valve 56 is in said closed position. As a result, the amount of bone cement dough 54 that continues to flow is reduced through the use of the three-way valve 56. The three-way valve 56 is screwed onto the dispensing tube 34 with the aid of wings 62. The front part of the tube 59 is connected to a hose 64 that merges into a trocar 66.

Upon further propulsion of the rod 44, the feed plunger 6 is punctured at the predetermined breakage site by the tip 45 of the rod 44. The feed plunger 6 cannot get out of the way in this context, since the transition between the receptacle 2 and the cartridge 1 in the tube-shaped container is provided in the form of a step that forms a limit stop for the mobility of the feed plunger 6 in the direction of the dispensing tube 34. In this context, the fragments 52 of the glass or plastic ampoule 3 can get jammed or be jammed between the feed plunger 6 and the step. The rod 44 also pushes, by way of its tip 45, through the remaining receptacle 2 of the device, in which the fragments 52 are situated. Finally, the rod 44 hits against the dispensing plunger 7 and pushes same in the direction of the dispensing tube 34.

The bone cement dough 54 can be dispensed through the hose 64 and the trocar 66. For this purpose, the dispensing plunger 7 is propelled in the direction of the dispensing tube 34 by the rod 44 (also refer to the detail view according to FIG. 10). When the three-way valve 56 is open, as is shown in FIG. 3D and in FIGS. 6 and 7, the bone cement dough 54 is expelled through the dispensing tube 34, through the three-way valve 56 and the passage 61, through the hose 64 and the trocar 66, and through a trocar tip 68 of the trocar 66 and can there be applied to the vertebrae of a patient or can theoretically be used for further processing. The three-way valve 56 can be operated in order to interrupt the flow of the bone cement dough 54. Pressurized bone cement dough 54 from the hose 64 and the trocar 66 can flow through the three-way valve 56 into the collecting container 60 without contaminating the surroundings. By this design, the flow of the bone cement dough 54 is interrupted rapidly.

The trocar 66 is directly connected to the hose 64, but can also be connected to the hose 64 by an adapter. The first embodiment in FIG. 5C shows a variant, in which a connector 72 connects a Luer system adapter 74 via a short hose 76 to the cartridge 1. The connector 72 can be screwed onto the dispensing tube 34 of the cartridge 1 with the aid of wings 78 in the way of a wing screw. For this purpose, the connector 72 comprises a matching internal thread.

The detail view of the detail magnification according to FIG. 6 of the valve system additionally shows that the tube 59 is connected to the hose 64 by an insert 80, which comprises a channel that aligns with the passage 61. For this purpose, the insert 80 is screwed into the tube 59. In order to ensure a pressure-tight connection, the hose 64 is crimped onto the insert 80 by a metal sleeve 82, and the tube 59 is sealed with respect to the internal wall of the dispensing tube 34 by two circumferential seals 84. The underside of the three-way valve 56 is secured with a stopper 86 such that the three-way valve 56 cannot be pulled easily from the valve seat 59 or tube 59. A draining channel 88 can be seen in the valve seat 59 in the sectional plane according to FIG. 7, which is perpendicular to the sectional plane according to FIG. 6 and is situated perpendicular to the passage 61, whereby, with the three-way valve 56 being in the closed position, the bone cement dough 54 can flow from the front side of the extended dispensing opening through said draining channel 88 into the collecting container 60.

The openings 39 also serve as visual markers that can be used to determine if the device is ready for use. This is the case because the pore filter 36 becomes visible through the openings 39 when the pore filter 36 is pushed forward due to the pressure of the bone cement dough 54 and, in the process, compresses the Styrofoam 40 in the cap 38. Thus, the user can recognize that the bone cement dough 54 is ready-mixed in the cartridge 1 and therefore is ready for use. At this point in time, the user can remove the cap 46, reconnect the extrusion device 43 to the device, and puncture the feed plunger 6 at the predetermined breakage site 9 with the tip 45 of the rod 44, and thus drive the dispensing plunger 7, and thus expel the bone cement dough 54 from the cartridge 1. Moreover, a suitable assembly, such as, for example, the trocar 66 with the hose 64 or the hose 76 with the Luer system adapter 74, can be connected to the external thread of the dispensing tube 34.

Figure 12A:
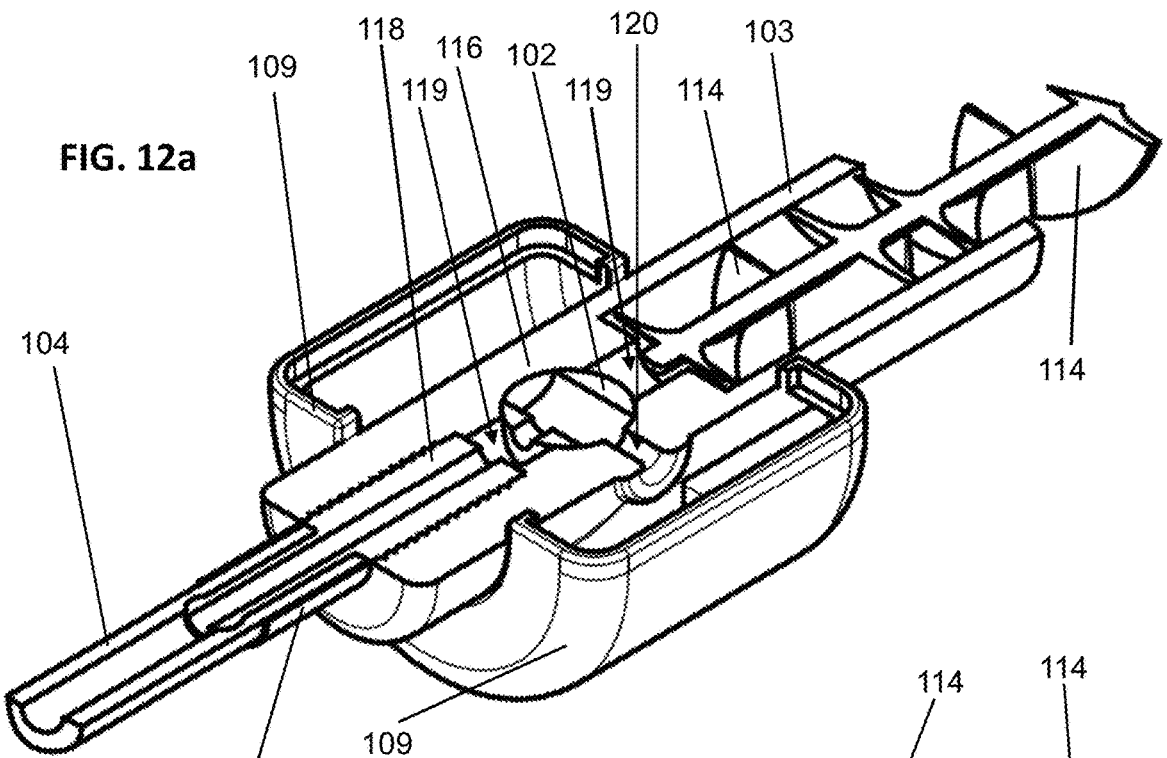
FIG. 12 includes FIGS. 12A and 12B which show two schematic perspective cross-sectional views through a valve system for an alternative device according to the invention, namely a three-way valve in a closed position (FIG. 12A) and in an open position (FIG. 12B)
Figure 12B:
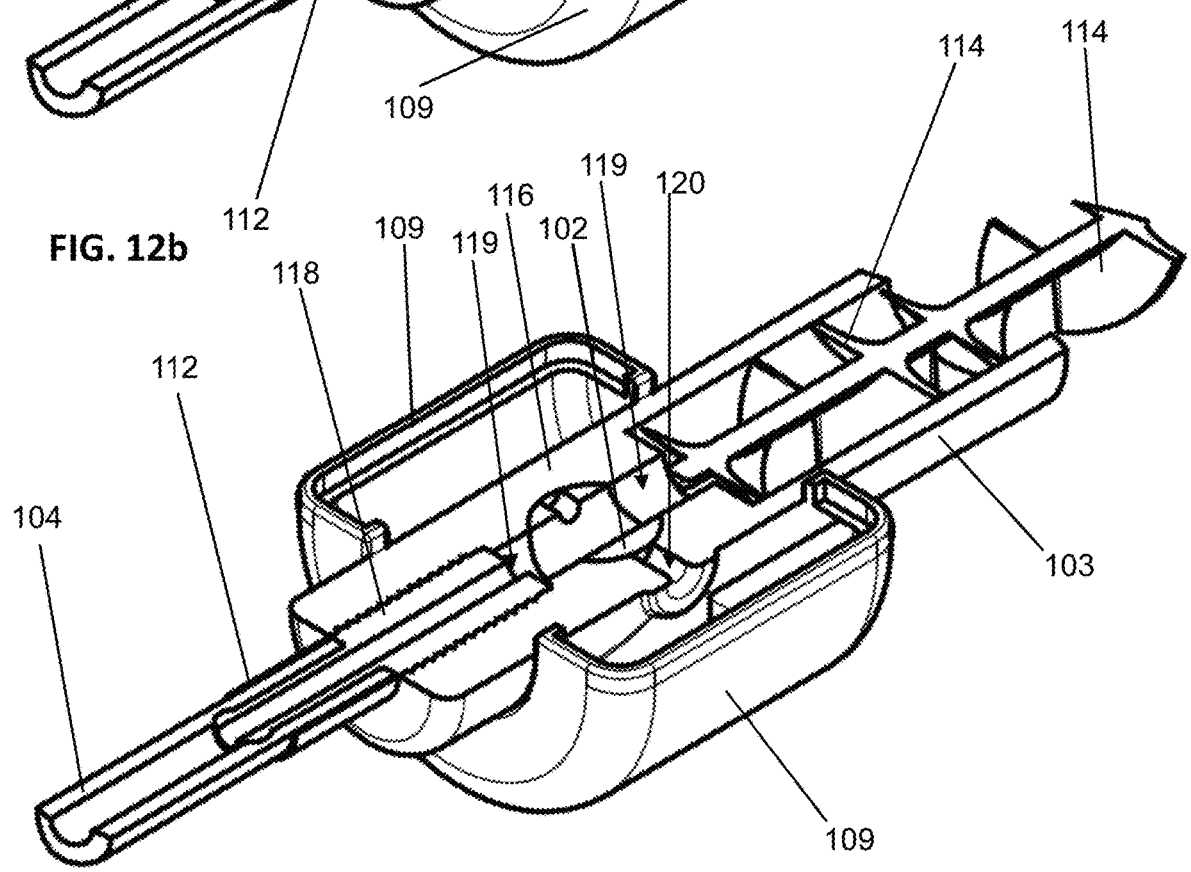
Figure 13A:
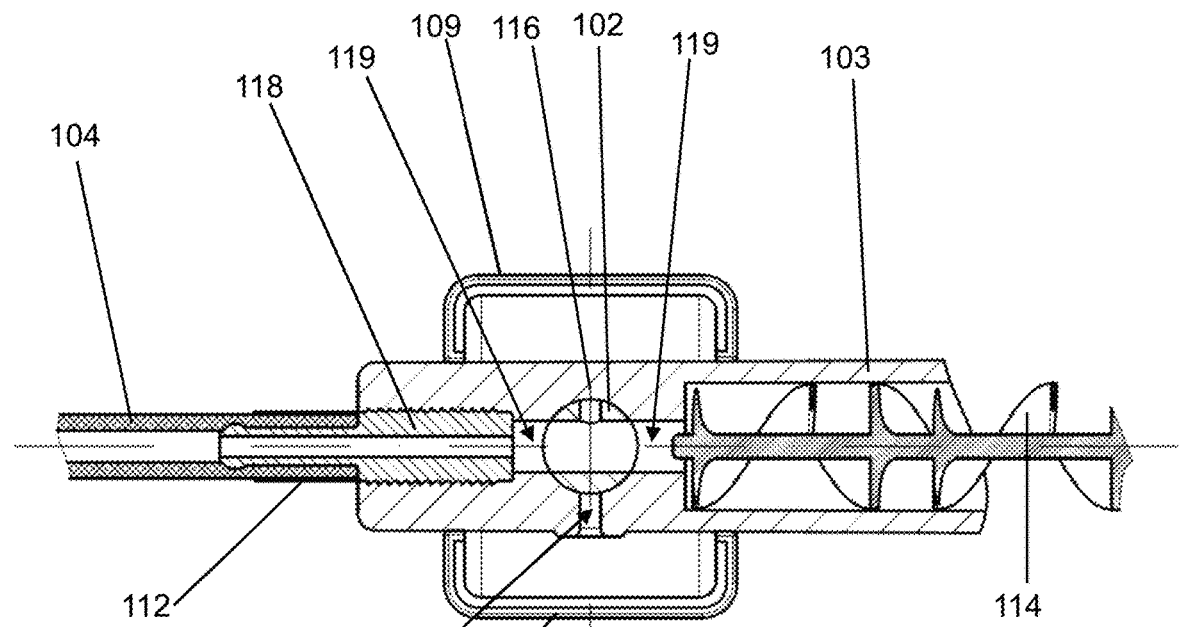
FIG. 13 includes FIGS. 13A and 13B which show two schematic cross-sectional top views through the valve system according to FIGS. 12A and 12B, namely the three-way valve in an open position (FIG. 13B) and in a closed position (FIG. 13A)
Figure 13B:
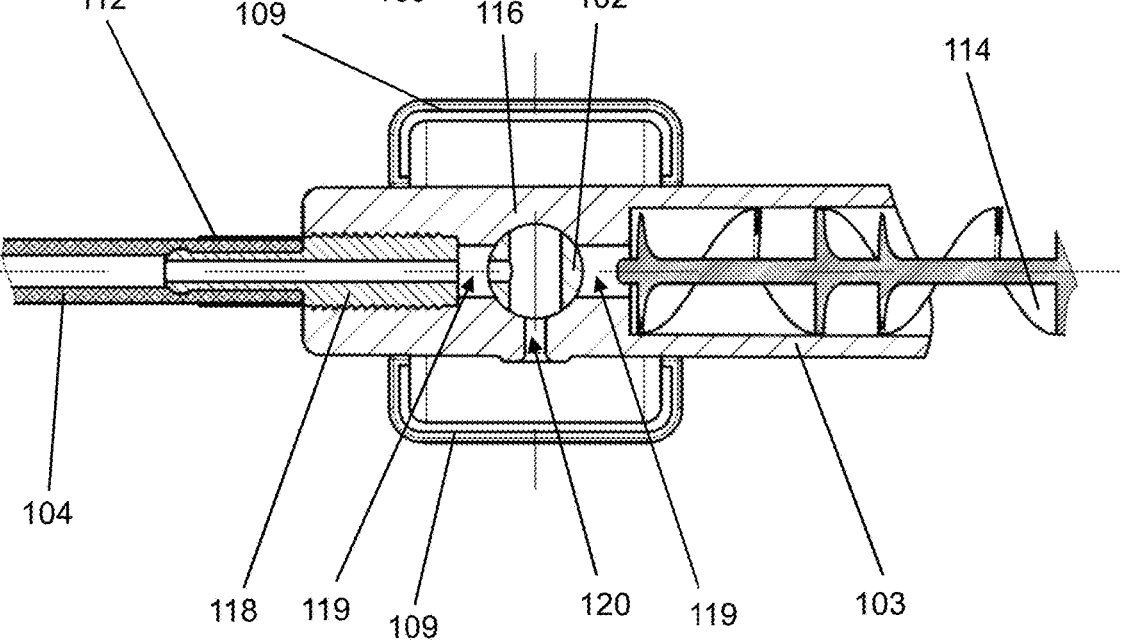

FIGS. 12 and 13 each show two schematic perspective cross-sectional views through an exemplary three-way valve 102 for a second alternative device according to the invention, namely the three-way valve 102 in a closed position (FIG. 12A and FIG. 13B) and in an open position (FIG. 12B and FIG. 13A) for illustration of the mode of function of the three-way valve 102 by way of the internal design.

The design of the alternative second device according to the invention is the same as that of the preceding first exemplary embodiment according to FIGS. 1 to 11 unless described otherwise or unless visualized otherwise in FIGS. 12 and 13.

A tube 103 is arranged as an extended dispensing opening on the front side of a cartridge (not shown in FIGS. 12 and 13, but provided as in the preceding exemplary embodiment). A hose 104 through which the bone cement dough (not shown in FIGS. 12 and 13) can be dispensed is secured to the valve system downstream of the valve system. To make sure that the bone cement dough cannot exit in an uncontrolled manner, a collecting container 109 is provided analogous to the embodiment according to FIGS. 6 and 7 and is intended to receive bone cement exiting from the three-way valve 102. By this design, contamination of the surroundings—i.e., in particular of the surgical area—by bone cement dough is prevented. The hose 104 is connected in a pressure-tight manner to the valve system by a sleeve 112 made of metal via a crimping connector.

A static mixer 114 that extends all the way up to the three-way valve 102 is situated on the inside of the tube 103. The static mixer 114 is used to mix the starting components of the bone cement and/or the pre-mixed bone cement dough, when these are pressed through the static mixer 114 in the tube 103.

The rotatable three-way valve 102 is sectioned in the plane of symmetry of the channels seen therein in the cross-sectional views according to FIGS. 12 and 13. Accordingly, the channels are cylindrical and continue in the cut-off part of the three-way valve 102 in mirror-symmetrical manner. The channels form a T-piece in the three-way valve 102. The three-way valve 102 sits in a fitting valve seat 116 that touches tightly against the three-way valve 102 and thus seals the channels, when these are rotated in the valve seat 116. The valve seat 116 has two passages 119 situated in it by which the larger through-going channel in the three-way valve 102 can be connected in a fluid-tight manner to the tube 103 on one side and to an insert 118 made of metal for attachment of the hose 104 on the other side.

A drain channel 120 connecting the valve seat 116 to the inside of the collecting container 109 that is closed towards the outside is situated perpendicular to the axis of the two passages 119. The valve seat 116 and the tube 103 are provided as a single part made of plastic material. In the open position of the three-way valve 102 (FIG. 12B, FIG. 13A), the large through-going channel is connected to the two passages 119 and the small perpendicular channel in the three-way valve 102 is closed through the valve seat 116. Accordingly, the bone cement dough from the cartridge can flow from the tube 103 through the three-way valve 102 and the insert 118 into the hose 104. In the closed position of the three-way valve 102 (FIG. 12A and FIG. 13B), one side of the large through-going channel is connected to the drain channel 120 to the internal space of the collecting container 109 and the smaller perpendicular channel is connected to the passage 119 to the hose 104, whereas the other passage 119 to the tube 103 is closed by the three-way valve 102. Accordingly, the bone cement dough can flow out of the hose 104 and, if applicable, out of a Luer system adapter (not shown) connected to the hose 104 and/or a connected trocar (not shown) into the collecting container 109. The pressure for this purpose results from an elastic deformation of the hose 104 and, if applicable, the trocar that has built up during the extrusion and/or while the bone cement dough was pressed through.

The three-way valve 102 can be rotated manually in the valve seat 116 by a control element (not shown), such as, for example, a T-handle (see the preceding exemplary embodiment). Being cylindrical on the outside, the three-way valve 102 is guided through a cylindrical borehole in the valve seat 116 and is connected to a stopper (not shown in FIGS. 12 and 13, but provided analogous to the preceding exemplary embodiment) on the side opposite from the control element (not shown) and thus is secured against dropping out or against being inadvertently pulled out of the valve seat 116.

Due to the design according to the invention, it is feasible to rapidly interrupt the flow of bone cement dough by rotating and thus closing the three-way valve 102 without large amounts of the bone cement dough continuing to flow through an application opening (not shown), into which the hose 104 or the trocar merges. Simultaneously, leakage of the bone cement dough and thus contamination of the surroundings or user is prevented by the collecting container 109 that takes up any excess bone cement dough. Moreover, the pressure in the rear side of the bone cement applicator, i.e., between the three-way valve 102 and the dispensing plunger of the cartridge, is maintained such that the flow of bone cement dough can be provided again rapidly after the three-way valve 102 is opened again without the pressure having to be built up again on the rear side of the device.

Figure 14:
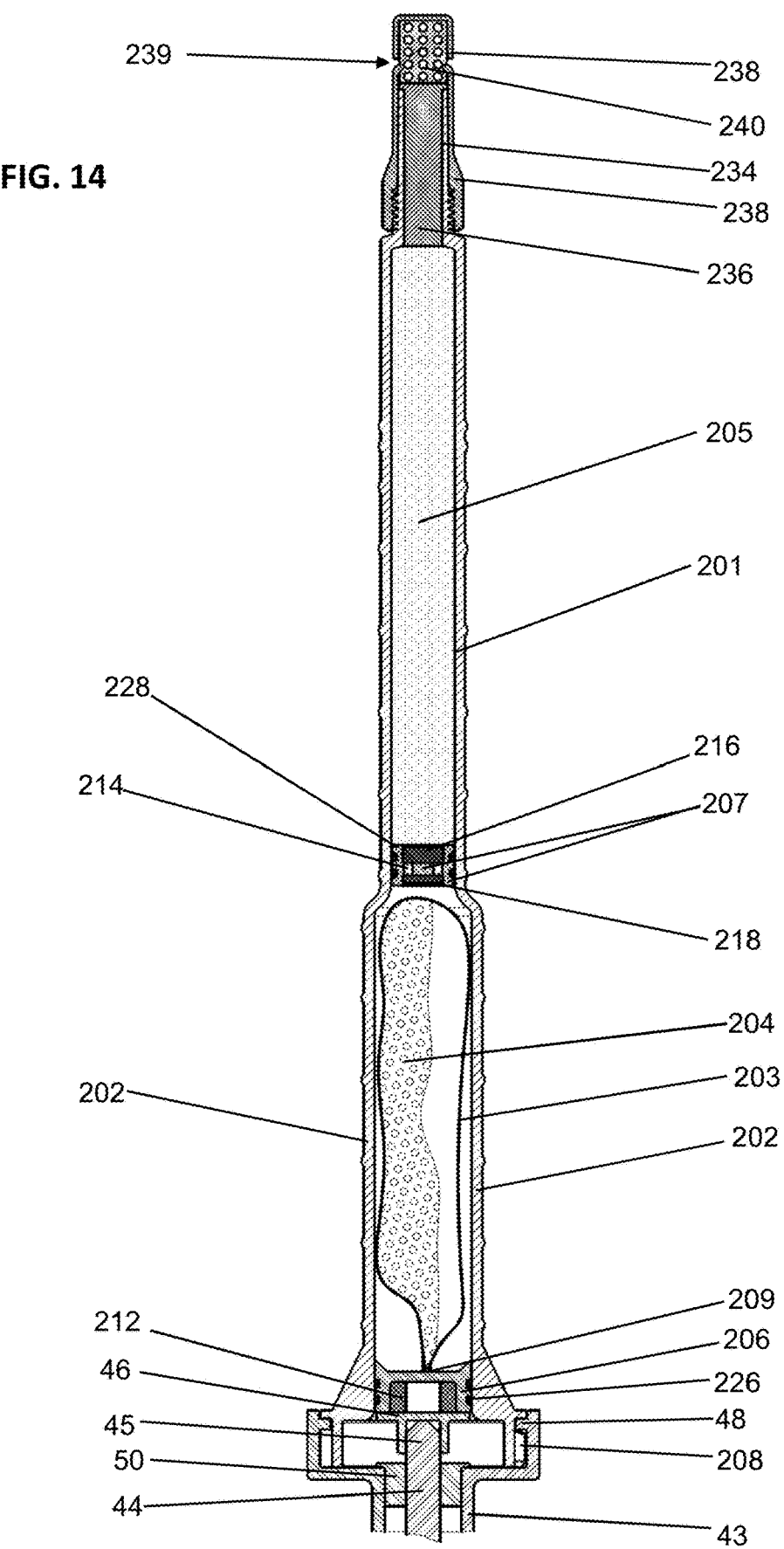
FIG. 14: shows a schematic cross-sectional view through a third exemplary embodiment according to the invention of a device for storage and mixing of a monomer liquid and a cement powder.

FIG. 14 shows a schematic cross-sectional view of a third alternative device according to the invention for storage and mixing of a monomer liquid 204 and a cement powder 205.

The design of the third alternative device according to the invention is the same as that of the first exemplary embodiment according to FIGS. 1 to 11 unless described otherwise or unless visualized otherwise in FIG. 14.

The device has a tube-shaped container made of plastics, which comprises a cartridge 201 with a cylindrical internal space as a front part (on the top in FIG. 14) and comprises a receptacle 202 for a film bag 203 made of plastics that can be coated by a metal, such as aluminium, as a rear part. The tube-shaped container is manufactured by injection molding. For this purpose, the receptacle 202 also comprises a cylindrical internal space into which the film bag 203 is plugged. The monomer liquid 204 is situated in the film bag 203. The cement powder 205 is filled or, preferably, pressed into the internal space of the cartridge 201. The monomer liquid 204 and the cement powder 205 are the starting components 204, 205 of a PMMA bone cement that can be produced with the device. With the aid of the film bag 203, the monomer liquid 204 can be stored in the receptacle 202 and therefore in the device for relatively long periods of times.

A feed plunger 206 made of plastics that is mobile in a longitudinal direction in the cylindrical internal space of the receptacle 202 is arranged in the receptacle 202. The feed plunger 206 is arranged in the area of the rear side of the receptacle 202. The film bag 203 can be compressed and thereby crushed or torn open in the receptacle 202 by the feed plunger 206 by pushing the feed plunger 206 in the direction of the front side, i.e., in the direction of the cartridge 201. The film bag 203 can be secured to the front side of the feed plunger 206 for this purpose. The feed plunger 206 comprises, on its front side, wipers by which shreds or residues of the film bag 203 can be wiped off the internal wall of the receptacle 202.

A dispensing plunger 207 made of plastics is arranged in a rear side (toward the bottom in FIG. 14) of the internal space of the cartridge 201. A securing means 208 is provided on a rear side of the receptacle 202 and can be used to connect the receptacle 202 to the extrusion device 43 (not shown in FIG. 14). Accordingly, the tube-shaped container can be secured to the extrusion device 43 by the receptacle 202. The securing means 208 is preferably well-suited and intended for the formation of a bayonet lock. By this design, the feed plunger 206, which is freely accessible from the rear side of the receptacle 202, is propellable in the direction of the front side by the extrusion device 43.

The feed plunger 206 is shaped like a short tube that is closed off by a planar wall on its front side that faces the film bag 203. The wall comprises, in the middle, a predetermined breakage site 209 that is accessible from the rear, i.e., from the rear side of the feed plunger 206, through a recess. The stabilization and sealing of the remaining feed plunger 206 is attained by a tube-shaped sleeve 212 that is also manufactured from plastics and is preferably provided in the form of a rubber cuff 212. Accordingly, the thickness of the material of the feed plunger 206 is reduced in the area of the predetermined breakage site 209. The film bag 203 can be secured to the feed plunger 206 in this location.

The cartridge 201 and the receptacle 202 have a one-part design in the form of a joint injection molded part. The receptacle 202 and the cartridge 201 are connected to each other in a liquid-permeable manner with respect to the monomer liquid 204 by a feedthrough 214 in the dispensing plunger 207. The feedthrough 214 through the dispensing plunger 207 merges through a pore filter 216, which is impermeable to the cement powder 205 but permeable to the monomer liquid 204, into the internal space of the cartridge 201.

A filter 218, by which the shreds and fragments of the film bag 203 can be retained, is arranged in the connection to the feedthrough 214 in the tube-shaped container. Instead of the filter 218 or in addition to the filter 218, a screen can be provided just as well or also. The filter 218 is arranged in the dispensing plunger 207.

The wall of the receptacle 202 is provided with multiple ventilation openings (not shown in FIG. 14) through which the internal space of the receptacle 202 can be sterilized with the aid of a sterilizing gas such as ethylene oxide. The ventilation openings are arranged analogous to the embodiment according to FIGS. 1 to 11 to be immediately adjacent to the feed plunger 206 such that the feed plunger 206 immediately closes the ventilation openings when it is being propelled in the direction of the cartridge 201. This prevents the monomer liquid 204 from exiting through the ventilation openings, after the film bag 203 in the receptacle 202 is opened.

The cylindrical feed plunger 206 has an external circumference that matches the cylindrical geometry of the internal space of the receptacle 202 and is sealed by two circumferential seals 226 in a liquid-tight manner with respect to the internal wall of the receptacle 202. Likewise, the dispensing plunger 207 is sealed in a liquid-tight manner with respect to the internal wall of the cartridge 201 by two circumferential seals 228. The purpose of said seals 226, 228 is to prevent monomer liquid 204 or bone cement from exiting in order to prevent contamination of the surroundings (the OR theater and the user). For this purpose, the seals 226, 228 can consist of rubber.

The front side of the cartridge 201 merges into a dispensing tube 234 that comprises an external thread. A pore filter 236 that is impermeable to the cement powder 205, but is permeable to gases, is arranged on the inside of the dispensing tube 234. A cap 238 is secured to the external thread of the dispensing tube 234, whereby the front part of the cap 238 is filled with a Styrofoam or foam 240. The cap 238 can be unscrewed from the dispensing tube 234. The cap 238 comprises lateral openings 239. Due to this design, the inside of the cartridge 201 and the cement powder 205 can be sterilized with the aid of ethylene oxide, since the openings 239 in the cap 238, the Styrofoam or foam 240, the pore filter 236, and the intervening spaces between the powder particles of the cement powder 205 are permeable to air. Concurrently, air can be pressed out of the receptacle through the cement powder 205, the pore filter 236, the Styrofoam or foam 240, and the openings 239 in the cap 238, when the feed plunger 206 is pressed in the direction of the receptacle 201.

The cement powder 205 is enclosed in the cartridge 201, since all openings 239 and feedthroughs 214 are closed with the aid of the pore filters 216, 236 such as to be impermeable to the cement powder 205. The content of the cartridge 201 can be sterilized by evacuation and rinsing with ethylene oxide in this context. Therefore, the device is also well-suited for long-term storage of the cement powder 205.

The procedure of a method according to the invention is discussed in the following on the basis of the third exemplary embodiment. At the outset of the method, the device is in the starting state that is also shown in FIG. 14. The tube-shaped container 201, 202 of the device is being inserted into the extrusion device 43 according to the invention in the form of a cartridge gun, and is secured to the extrusion device 43 by the securing means 208.

The extrusion device 43 comprises the rod 44 that can be propelled linearly. Only the front part of the extrusion device 43, by which it differs from conventional extrusion devices, is shown. The extrusion device 43 also comprises a handle and a tilting lever (not shown in FIG. 14) for manually driving the rod 44 of the extrusion device 43, like conventional manually driven extrusion devices. The device is secured to the extrusion device 43 by the securing means 208. The rod 44 ends, on its front side, in the tip 45, which can initially be covered by the cap 46 which can be punctured. Preferably, it is just as well to omit the cap 46, since the film bag 203 is flexible enough and does not produce stable shards, such as a glass ampoule would, such that the motion of the feed plunger 206 is not counteracted by a sufficiently strong force causing the feed plunger 206 to be punctured at the predetermined breakage site 209 before it reaches the step-shaped limit stop between the receptacle 202 and the cartridge 201. The rod 44 then pushes, by the cap 46, onto the sleeve 212 and/or rubber cuff 212 of the feed plunger 206 or, by the tip 45, onto the rear side of the feed plunger 206, when the extrusion device 43 pushes the rod 44 into the receptacle 202. For this purpose, the extrusion device 43 is connected to the rear side of the receptacle 202 by the opposite securing means 48. For this purpose, the rod 44 is supported such as to be linearly mobile with respect to the bearing 50 and, through it, with respect to the opposite securing means 48 and therefore with respect to the receptacle 202.

Operating the extrusion device 43 propels the rod 44 and, through the rod 44, the feed plunger 6 in the direction of the cartridge 1. Since the film bag 203 touches against the dispensing plunger 207 on its front side, the internal space of the receptacle 202 decreases in size and the film bag 203 bursts or tears and the monomer liquid 204 exits from the film bag 203 into the internal space of the receptacle 202. The dispensing plunger 207 cannot be pushed in the direction of the pore filter 236 by the film bag 203 when the cement powder 205 is dry, i.e., not wetted by the monomer liquid 204, since the dry cement powder 205 does not flow and blocks any motion of the dispensing plunger 207. Supernatant air from the receptacle 202 is pushed through the filter 218, the feedthrough 214, the pore filter 216, through the intervening spaces between the particles of the cement powder 205, through the pore filter 236, through the foam 240, and out of the openings 239 in the cap 238 out of the device.

Lastly, only shreds and residues of the film bag 203 remain and are retained by the filter 218 and remain in the tube-shaped container. The monomer liquid 204 is pressed through the filter 218, the feedthrough 214, and the pore filter 216 into the cement powder 205 and there starts to react with the cement powder 205 such that the bone cement dough 54 is produced from the mixture 54. As soon as the bone cement dough 54 is produced, the pore filter 36 is driven forward by the pressure acting on the bone cement dough 54 due to the pressure acting on the dispensing plunger 207, and compresses the foam 240. When the pore filter 236 slides forward, it becomes visible to the user from the outside through the opening 239 in the cap 238. This situation is shown analogously in FIG. 4. For this purpose, the pore filter 236 preferably differs in color and brightness from the foam 240. For example, the foam 240 can be white and the pore filter 236 can be red.

In this state, the cap 238 with the pore filter 236 and the foam 240 is unscrewed and, instead, an extended dispensing opening is screwed onto the dispensing tube 234. The extended dispensing opening can preferably comprise a three-way valve analogous to the first or second embodiment. Likewise, a hose and/or a trocar can be connected to the dispensing tube 234. The rod 44 is driven further and, in the process, its tip 45 punctures the feed plunger 206, which is blocked by the step between the cartridge 201 and the receptacle 202, at the predetermined breakage site 209 and, if applicable, punctures the cap 46 earlier. The shreds and/or residues of the film bag 203 are pushed aside in this context. The tip 45 of the rod 44 hits against the dispensing plunger 207.

The bone cement dough 54 can be dispensed through the hose 64 and the trocar 66 or through the dispensing tube 234. For this purpose, the dispensing plunger 207 is propelled in the direction of the dispensing tube 234 by the rod 44. The bone cement dough 54 from the inside of the cartridge 201 is expelled either directly through the dispensing tube 234 or, if the three-way valve 102 is open, through the dispensing tube 234, through the three-way valve 102, through the hose 64, and the trocar 66 and can there be applied to the vertebrae of a patient or can theoretically be used for further processing. The three-way valve 102 can be operated, if applicable, in order to interrupt the flow of the bone cement dough 54.

The openings 239 also serve as visual markers that can be used to determine if the device is ready for use. This is the case because the pore filter 236 becomes visible through the openings 239 when the pore filter 236 is pushed forward due to the pressure of the bone cement dough 54 and, in the process, compresses the Styrofoam 240 in the cap 238. Thus, the user can recognize that the bone cement dough 54 is ready-mixed in the cartridge 201 and therefore is ready for use. At this point in time, the user can secure a suitable assembly, such as, for example, the trocar 66 with the hose 64, to the external thread of the dispensing tube 234 and puncture the feed plunger 206 at the predetermined breakage site 209 with the tip 45 of the rod 44, and thus drive the dispensing plunger 207, and thus expel the bone cement dough 54 from the cartridge 201.

The features of the invention disclosed in the preceding description and in the claims, figures, and exemplary embodiments, can be essential for the implementation of the various embodiments of the invention both alone and in any combination.

The invention claimed is:

1. A device for storage of a monomer liquid and a cement powder as starting components of a bone cement dough and for mixing of the bone cement dough from the starting components, and for dispensing the mixed bone cement dough, the device comprising:
    a tube-shaped container that forms, on its rear side, a receptacle with a cylindrical internal space, in which a monomer liquid container is arranged, whereby the monomer liquid container contains the monomer liquid, and the container forms, on its front side, a cartridge with a cylindrical internal space that contains the cement powder;
    a feed plunger which is movable in a longitudinal direction of the receptacle and which is accessible from a rear side of the receptacle, whereby the feed plunger is arranged in the internal space of the receptacle; and
    a dispensing plunger which is movable in a longitudinal direction in the internal space of the cartridge, whereby the dispensing plunger is arranged between the monomer liquid container and the cement powder in the internal space of the cartridge, whereby
    the internal space of the receptacle and the internal space of the cartridge are connected to each other through a connection that is permeable to the monomer liquid and that is permeable to gases, but is impermeable to the cement powder, and whereby
    the feed plunger is configured to be punctured, from the rear side, by a rod when a motion of the feed plunger in the direction of the front side of the container is blocked, whereby the dispensing plunger is configured to be propelled by propelling the rod further through the blocked and punctured feed plunger in the direction of a front side of the cartridge.

2. The device according to claim 1, wherein the tube-shaped container has a one-part design, whereby the receptacle and the cartridge are a one-part thermoplastic resin body, whereby the container is manufactured using an injection molding process.

3. The device according to claim 1, wherein a cross-sectional surface area of the internal space of the cartridge is smaller than a cross-sectional surface area of the internal space of the receptacle.

4. The device according to claim 1 further comprising a securing means for securing an extrusion device, the securing means arranged on the rear side of the receptacle.

5. The device according to claim 1 further comprising a limit stop on an inside of the container that limits the motion of the feed plunger in the direction of the front side, whereby the limit stop limits the motion such that the feed plunger cannot be fully pressed out of the receptacle, whereby the limit stop is formed as a step arising from different shapes or different cross-sections of the cylindrical internal space of the cartridge and the cylindrical internal space of the receptacle at a transition between the receptacle and the cartridge.

6. The device according to claim 1 wherein the connection is arranged in the dispensing plunger and connects a front side of the dispensing plunger to a rear side of the dispensing plunger that faces the monomer liquid container.

7. The device according to claim 1 further comprising a filter that is permeable to gases and the monomer liquid, but is impermeable to the cement powder, and is arranged at a merging site of the connection into the internal space of the cartridge.

8. The device according to claim 1 wherein the cement powder touches against a front side of the dispensing plunger, whereby the cement powder is pressed into the internal space of the cartridge.

9. The device according to claim 1 wherein the cartridge comprises, on the front side, a dispensing opening that is closed by a closure, whereby the bone cement dough is adapted to be extruded from the cartridge through the dispensing opening, if the dispensing opening is open, and whereby the closure is permeable to gases and impermeable to the cement powder.

10. The device according to claim 1 further comprising a dispensing tube or a flexible hose with a trocar is secured to the front side of the cartridge, whereby the bone cement dough is adapted to be extruded through the dispensing tube or the flexible hose and the trocar, whereby a manually closable valve element, which is configured to control the flow of bone cement dough, is arranged on the dispensing tube or the flexible hose.

11. The device according to claim 1 wherein the feed plunger is configured to be punctured from a rear side by the rod comprising a tip or an edge, if the feed plunger is blocked from moving further in the direction of the front side of the tube-shaped container.

12. The device according to claim 11 wherein the feed plunger is configured to be punctured with a force of at least 1 kN.

13. The device according to claim 1 wherein the feed plunger has a maximum thickness in an area of a contact surface of the rod of at most 4 mm.

14. The device according to claim 1 wherein a cross-section of the internal space of the cartridge is at most 4 cm$^2$.

15. The device according to claim 1 wherein the monomer liquid container is a glass ampoule, a plastic ampoule, a plastic film bag or an aluminium-plastic compound bag.

16. The device according to claim 1 wherein a volume of the monomer liquid in the monomer liquid container is at least as large as a volume of air-filled intervening spaces between the cement powder particles in the cartridge, and is at least as large as a volume of the liquid conduits between the internal space of the cartridge and the internal space of the receptacle plus the volume of the air-filled intervening spaces between the cement powder particles in the cartridge.

17. The device according to claim 1 wherein a wall of the receptacle has at least one ventilation opening, whereby the at least one ventilation opening connects the internal space of the receptacle, in which the monomer liquid container is arranged, to the surroundings, whereby the at least one ventilation opening is arranged sufficiently close to the feed plunger such that it is closed by a motion of the feed plunger in the direction of a front side of the receptacle before the monomer liquid container is opened through the motion of the feed plunger.

18. The device according to claim 1 further comprising a screen or a porous disk that is permeable to gases and liquids provided on a front side of the receptacle in the connection to the cartridge.

19. The device according to claim 1 further comprising:
a three-way valve that is operable from outside and is arranged in the flow direction of the bone cement dough in a conduit downstream from the cartridge; and
a collecting container for reception of bone cement dough arranged on the three-way valve, whereby the conduit merges into an application opening that is arranged on an end of the conduit that faces away from the cartridge, whereby the three-way valve when in a first position provides a fluid connection between the application opening and the cartridge and closes a discharge channel toward the collecting container and, when in a second position provides a fluid connection between the application opening and the collecting container and closes a passage to the cartridge.

20. The device according to claim 1 wherein the monomer liquid container is configured to be opened on the inside of the receptacle through a motion of the feed plunger in the direction of a front side of the receptacle, and can be opened by breaking or tearing.

21. The device according to claim 1 wherein the feed plunger comprises, on the rear-side face, a cylindrical recess for the rod of an extrusion device, in which a rubber cuff is arranged as a sealing element or in which a plastic or metal disk is arranged as sealing element that is configured to be plastically deformed and punctured by the rod.

22. A method for the production of a bone cement dough, in particular of a pasty polymethylmethacrylate bone cement dough, whereby the bone cement dough is produced from a cement powder and a monomer liquid through the use of a device, whereby the device comprises a tube-shaped container that forms, on its rear side, a receptacle with a cylindrical internal space, in which a monomer liquid container with the monomer liquid in it is arranged, and the container forms, on its front side, a cartridge with a cylindrical internal space that contains the cement powder, the method comprising the following steps proceeding in the order given:
a) inserting the device in an extrusion device, whereby the extrusion device comprises a rod that is configured to be propelled in an axial direction;
b) propelling a feed plunger, supported such as to be mobile in the receptacle on a rear side thereof, in the direction of the cartridge by the rod, whereby the motion of the feed plunger opens the monomer liquid container and presses the monomer liquid from the receptacle into the cartridge, whereby the cement powder mixes with the monomer liquid in the internal space of the cartridge;
c) blocking the motion of the feed plunger in the direction of the front side of the container;
d) puncturing with the rod the feed plunger and after puncturing the feed plunger hitting with the rod a dispensing plunger that is supported in the cartridge such as to be mobile; and
e) propelling the dispensing plunger in the direction of the front side of the cartridge by the rod, while the rod runs through the blocked and punctured feed plunger, whereby the mixture of cement powder and monomer liquid is expelled from the cartridge as bone cement dough due to the motion of the dispensing plunger.

23. The method according to claim 22, wherein the feed plunger is movable in a longitudinal direction of the receptacle and which is accessible from a rear side of the receptacle, whereby the feed plunger is arranged in the internal space of the receptacle, and the device further comprises a dispensing plunger which is movable in a longitudinal direction in the internal space of the cartridge, whereby the dispensing plunger is arranged between the monomer liquid container and the cement powder in the internal space of the cartridge, whereby the internal space of the receptacle and the internal space of the cartridge are connected to each other through a connection that is permeable to the monomer liquid and that is permeable to gases, but is impermeable to the cement powder, and whereby the feed plunger is configured to be punctured, from the rear side, by the rod when a motion of the feed plunger in the direction of the front side of the container is blocked, whereby the dispensing plunger is configured to be propelled by propelling the rod further through the blocked and punctured feed plunger in the direction of a front side of the cartridge.

24. The method according to claim 22, wherein the device comprises a bracket for securing the device and wherein the rod comprises, on a front side, a hard tip or an edge for puncturing a blocked feed plunger of the device, whereby a removable or pierceable cap with a level front side is arranged on the tip or edge.

25. The method according to claim 22, wherein the rod comprises, on the front side, a hard tip or edge for puncturing the blocked feed plunger of the device, whereby, in step a), a removable cap with a level front side is arranged on the tip or edge, and the cap is removed from the tip or edge after step c), and the rod is driven into the feed plunger by the tip or edge, whereby the device is removed from the extrusion device earlier and the device is re-inserted into the extrusion device after removing the cap from the tip or edge.

26. The method according to claim 22, further comprising moving or pushing a closure in or out of a dispensing opening on the front side of the cartridge before step c) or in step c) by the pressure acting on the mixture of cement powder and monomer liquid, whereby the closure is then removed from the dispensing opening and an extended dispensing tube or a hose with a trocar is secured to the front side of the cartridge or the cap is removed from the tip or edge of the rod.

27. The method according to claim 22, further comprising pushing the crushed or slit-open or burst-open monomer liquid container together in step b) and simultaneously pushing gas from the receptacle through a connection into the cartridge through the cement powder in the cartridge to the outside, and whereby, in step d), the rod is driven through the feed plunger and displaces the fragments of the monomer liquid container.

28. The method according to claim 22, further comprising in step d) right before the application of the bone cement dough, connecting a trocar with a hose to the cartridge on the front side of the cartridge on a dispensing opening and subsequently extruding the bone cement dough through the hose and the trocar.

* * * * *